US011845763B2

United States Patent
Pelecanou Zampara et al.

(10) Patent No.: US 11,845,763 B2
(45) Date of Patent: Dec. 19, 2023

(54) TRICARBONYL COMPLEXES OF TRANSITION METALS WITH BENZO-HETEROCYCLIC DERIVATIVES OF THE CYCLOPENTADIENYL ANION

(71) Applicants: National Centre For Scientific Research "Demokritos", Agia Paraskevi (GR); Maria Pelecanou Zampara, Athens (GR); Marina Sagnou, Athens (GR); Minas Papadopoulos, Attiki (GR); Ioannis Pirmettis, Athens (GR)

(72) Inventors: Maria Pelecanou Zampara, Athens (GR); Marina Sagnou, Athens (GR); Minas Papadopoulos, Attiki (GR); Ioannis Pirmettis, Athens (GR); Barbara Mavroidi, Moschatos (GR); Antonio Shegani, Krines-Velo (GR)

(73) Assignee: NATIONAL CENTRE FOR SCIENTIFIC RESEARCH "DEMOKRITOS", Agia Paraskevi (GR)

( * ) Notice: Subject to any disclaimer, the term of this patent is extended or adjusted under 35 U.S.C. 154(b) by 132 days.

(21) Appl. No.: 17/040,117

(22) PCT Filed: Mar. 22, 2019

(86) PCT No.: PCT/EP2019/057235
§ 371 (c)(1),
(2) Date: Sep. 22, 2020

(87) PCT Pub. No.: WO2019/180200
PCT Pub. Date: Sep. 26, 2019

(65) Prior Publication Data
US 2021/0024555 A1    Jan. 28, 2021

(30) Foreign Application Priority Data
Mar. 22, 2018  (GR) ............... 20180100128

(51) Int. Cl.
*C07F 13/00*  (2006.01)
*A61K 51/04*  (2006.01)

(52) U.S. Cl.
CPC ........ *C07F 13/005* (2013.01); *A61K 51/0453* (2013.01)

(58) Field of Classification Search
CPC .......................... C07F 13/005; A61K 51/0453
USPC ....................................................... 424/1.65
See application file for complete search history.

(56) References Cited

FOREIGN PATENT DOCUMENTS

WO    WO-03086476 A1 * 10/2003   ......... A61K 51/0421

OTHER PUBLICATIONS

Worachartcheewan et al. Chem. Pap. 2013, 67, 1462-1473. (Year: 2013).*
Torres-Gomez et al. Bioorg. Med. Chem. Lett. 2008, 18, 3147-3151. (Year: 2008).*
Can et al. Chem. Biodiv. 2012, 19, 1849-1866. (Year: 2012).*
Hora et al. Metab. Brain Dis. 2016, 31, 225-237/ (Year: 2016).*
Li et al. J. Chem. Soc., Dalton trans., 1998, 3791-3799. (Year: 1998).*
Hausner et al. Abs. Pap. Am. Chem. Soc. 2003, 226, 290. (Year: 2003).*
International Search Report and Written Opinion of the International Searching Authority, issued in PCT/EP2019/057235, dated Jul. 17, 2019; ISA/EP.
International Preliminary Report on Patentability of the International Searching Authority, issued in PCT/EP2019/057235, dated Jun. 9, 2020; ISA/EP.
Patricia Toro et al: "Organometallic benzimidazoles: Synthesis, characterization and antimalarial activfity" Inorganic Chemistry Communications, Elsevier Amsterdam, NL, vol. 35, pp. 126-129 (Jun. 19, 2013).
Marina Sagnou et al "Remarkable Brain Penetration of Cyclopentadienyl M(CO) 3 + (M=99m Tc, Re) Derivatives of Benzothiazole and Benzimidazole Paves the Way for Their Application as Diagnostic, with Single-Photon-Emission Computed Tomography (SPECT), and Therapeutic Agents for Alzheimer's Disease", Journal of Medicinal Chemistry, vol. 62, No. 5, pp. 2638-2650 (Feb. 15, 2019).
Kiritsis, Christos, et al. "2-(4'-Aminophenyl)Benzothiazole Labeled with 99mTc-Cyclopentadienyl for Imaging β-Amyloid Plaques." *ACS Medicinal Chemistry Letters*, vol. 8, No. 10, 2017, pp. 1089-1092.

(Continued)

*Primary Examiner* — Michael G. Hartley
*Assistant Examiner* — Sean R Donohue
(74) *Attorney, Agent, or Firm* — Harness, Dickey & Pierce, P.L.C.

(57) ABSTRACT

Complex compounds of transition metals according to formula (1) wherein the $M(CO)_3^+$ tricarbonyl-metal core forms a complex with the cyclopentadienyl anion linked to heterocyclic moieties of the benzothiazole, benzimidazole and benzoxazole families. The compounds exhibit high blood-brain barrier permeability and can be used in the diagnosis and/or treatment of diseases of the Central Nervous System.

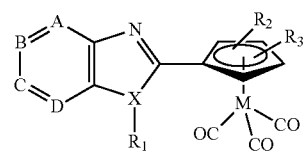

13 Claims, 4 Drawing Sheets

(56) References Cited

OTHER PUBLICATIONS

Pardridge, William M. "The Blood-Brain Barrier: Bottleneck in Brain Drug Development." *Neurotherapeutics*, vol. 2, No. 1, 2005, pp. 3-14.
Wager, Travis T., et al. "Strategies to Optimize the Brain Availability of Central Nervous System Drug Candidates." *Expert Opinion on Drug Discovery*, vol. 6, No. 4, 2011, pp. 371-381.
Pardridge, William M. "Alzheimer's Disease Drug Development and the Problem of the Blood-Brain Barrier." *Alzheimer's & Dementia*, vol. 5, No. 5, 2009, pp. 427-432.
Hardy, John. "A Hundred Years of Alzheimer's Disease Research." *Neuron*, vol. 52, No. 1, 2006, pp. 3-13.
Selkoe, D. J., & Hardy, J. (2016a). The amyloid hypothesis of Alzheimer's disease at 25 years. *EMBO Molecular Medicine*, 8(6), 595-608.
Chen, Kaihua, and Mengchao Cui. "Recent Progress in the Development of Metal Complexes as β-Amyloid Imaging Probes in the Brain." *MedChemComm*, vol. 8, No. 7, 2017, pp. 1393-1407.
Montine, Thomas J., et al. "National Institute on Aging-Alzheimer's Association Guidelines for the Neuropathologic Assessment of Alzheimer's Disease: A Practical Approach." *Acta Neuropathologica*, vol. 123, No. 1, 2011, pp. 1-11.
McKhann, Guy M., et al. "The Diagnosis of Dementia Due to Alzheimer's Disease: Recommendations from the National Institute on Aging-Alzheimer's Association Workgroups on Diagnostic Guidelines for Alzheimer's Disease." *Alzheimer's & Dementia*, vol. 7, No. 3, 2011, pp. 263-269.
Hardy, J. "The Amyloid Hypothesis of Alzheimer's Disease: Progress and Problems on the Road to Therapeutics." *Science*, vol. 297, No. 5580, 2002, pp. 353-356.
Johnson, K. A., et al. "Appropriate Use Criteria for Amyloid PET: A Report of the Amyloid Imaging Task Force, the Society of Nuclear Medicine and Molecular Imaging, and the Alzheimer's Association." *Journal of Nuclear Medicine*, vol. 54, No. 3, 2013, pp. 476-490.
Dubois, Bruno, et al. "Timely Diagnosis for Alzheimer's Disease: A Literature Review on Benefits and Challenges." *Journal of Alzheimer's Disease*, edited by Andrew Saykin, vol. 49, No. 3, 2015, pp. 617-631.
Ono, Masahiro, and Hideo Saji. "Recent Advances in Molecular Imaging Probes for β-Amyloid Plaques." *MedChemComm*, vol. 6, No. 3, 2015, pp. 391-402.
Bernard, Jonathan, et al. "Aqueous Synthesis of Derivatized Cyclopentadienyl Complexes of Technetium and Rhenium Directed toward Radiopharmaceutical Application." *Inorganic Chemistry*, vol. 42, No. 4, 2003, pp. 1014-1022.
Cui, M. "Past and Recent Progress of Molecular Imaging Probes for β-Amyloid Plaques in the Brain." *Current Medicinal Chemistry*, vol. 21, No. 1, 2013, pp. 82-112.
Li, Zijing, et al. "Novel Cyclopentadienyl Tricarbonyl Complexes Of99mTc Mimicking Chalcone as Potential Single-Photon Emission Computed Tomography Imaging Probes for β-Amyloid Plaques in Brain." *Journal of Medicinal Chemistry*, vol. 56, No. 2, 2013, pp. 471-482.
Jia, Jianhua, et al. "2-Phenylbenzothiazole Conjugated with Cyclopentadienyl Tricarbonyl [CpM(CO)3] (M=Re,99mTc) Complexes as Potential Imaging Probes for β-Amyloid Plaques." *Dalton Transactions*, vol. 44, No. 14, 2015, pp. 6406-6415.
Jia, Jianhua, Kaixiang Zhou, et al. "2-Arylbenzothiazoles Labeled with [CpRe/ 99m Tc(CO) 3 ] and Evaluated as β-Amyloid Imaging Probes." *European Journal of Medicinal Chemistry*, vol. 124, 2016, pp. 763-772.
Kim, Seung Hyun, et al. "Beyond Symptomatic Effects: Potential of Donepezil as a Neuroprotective Agent and Disease Modifier in Alzheimer's Disease." *British Journal of Pharmacology*, vol. 174, No. 23, 2017, pp. 4224-4232.
Walsh, D. M., & Selkoe, D. J. (2007). A? Oligomers ? a decade of discovery. *Journal of Neurochemistry*, 101(5), 1172-1184.
Belluti, Federica, et al. "Small-Molecule Inhibitors/Modulators of Amyloid-β Peptide Aggregation and Toxicity for the Treatment of Alzheimer's Disease: A Patent Review (2010-2012)." *Expert Opinion on Therapeutic Patents*, vol. 23, No. 5, 2013, pp. 581-596.
Ansari, Niloufar, and Fariba Khodagholi. "Natural Products as Promising Drug Candidates for the Treatment of Alzheimer's Disease: Molecular Mechanism Aspect." *Current Neuropharmacology*, vol. 11, No. 4, 2013, pp. 414-429.
Campagna, Francesco, et al. "Synthesis and Biophysical Evaluation of Arylhydrazono-1H-2-Indolinones as β-Amyloid Aggregation Inhibitors." *European Journal of Medicinal Chemistry*, vol. 46, No. 1, 2011, pp. 275-284.
Datki, Zsolt, et al. "Method for Measuring Neurotoxicity of Aggregating Polypeptides with the MTT Assay on Differentiated Neuroblastoma Cells." *Brain Research Bulletin*, vol. 62, No. 3, 2003, pp. 223-229.
Banks, William A. "Drug Delivery to the Brain in Alzheimer's Disease: Consideration of the Blood-Brain Barrier." *Advanced Drug Delivery Reviews*, vol. 64, No. 7, 2012, pp. 629-639.
Stimpfel, M., and I. Virant-Klun. "Cancer Incidence and Mortality Worldwide: Sources, Methods and Major Patterns in GLOBOCAN 2012." *Journal of Cancer Stem Cell Research*, vol. 4, No. 3, 2016, p. 1.
Ostrom, Quinn T., et al. "American Brain Tumor Association Adolescent and Young Adult Primary Brain and Central Nervous System Tumors Diagnosed in the United States in 2008-2012." *Neuro-Oncology*, vol. 18, No. suppl 1, 2015, pp. i1-50.
Fortin, D. "The Blood-Brain Barrier: Its Influence in the Treatment of Brain Tumors Metastases." *Current Cancer Drug Targets*, vol. 12, No. 3, 2012, pp. 247-259.
Pitz, Marshall W., et al. "Tissue Concentration of Systemically Administered Antineoplastic Agents in Human Brain Tumors." *Journal of Neuro-Oncology*, vol. 104, No. 3, 2011, pp. 629-638.
Antonadou, D., Paraskevaidis, M., Sarris, G., Coliarakis, N., Economou, I., Karageorgis, P., & Throuvalas, N. (2002). Phase II Randomized Trial of Temozolomide and Concurrent Radiotherapy in Patients With Brain Metastases. *Journal of Clinical Oncology*, 20(17), 3644-3650.
Weidle, U. H., Niewöhner, J., & Tiefenthaler, G. (2015). The Blood-Brain Barrier Challenge for the Treatment of Brain Cancer, Secondary Brain Metastases, and Neurological Diseases. *Cancer genomics & proteomics*, 12(4), 167-177.
Santra, Amburanjan, et al. "Use of 99m-Technetium-Glucoheptonate as a Tracer for Brain Tumor Imaging: An Overview of Its Strengths and Pitfalls." *Indian Journal of Nuclear Medicine*, vol. 30, No. 1, 2015, p. 1.
Gao, Huile, and Xinguo Jiang. "Progress on the Diagnosis and Evaluation of Brain Tumors." *Cancer Imaging*, vol. 13, No. 4, 2013, pp. 466-481.
Deutsch, Edward, et al. "The Chemistry of Rhenium and Technetium as Related to the Use of Isotopes of These Elements in Therapeutic and Diagnostic Nuclear Medicine." *International Journal of Radiation Applications and Instrumentation. Part B. Nuclear Medicine and Biology*, vol. 13, No. 4, 1986, pp. 465-477.
Bradshaw, T., and A. Westwell. "The Development of the Antitumour Benzothiazole Prodrug, Phortress, as a Clinical Candidate." *Current Medicinal Chemistry*, vol. 11, No. 8, 2004, pp. 1009-1021.
Shrivastava, Neelima, et al. "Benzimidazole Scaffold as Anticancer Agent: Synthetic Approaches and Structure-Activity Relationship." *Archiv Der Pharmazie*, vol. 350, No. 6, 2017, p. e201700040.
Xiang, P., Zhou, T., Wang, L., Sun, C.-Y., Hu, J., Zhao, Y.-L., & Yang, L. (2012). Novel Benzothiazole, Benzimidazole and Benzoxazole Derivatives as Potential Antitumor Agents: Synthesis and Preliminary in Vitro Biological Evaluation. *Molecules*, 17(1), 873-883.
Nakamura, Kayoko, et al. "The Behavior Of 99mTc-Hexamethylpropyleneamineoxime (99mTc-HMPAO) in Blood and Brain." *European Journal of Nuclear Medicine*, vol. 15, No. 2, 1989, pp. 100-107.
Vanbilloen, Hubert P., et al. "Importance of the Two Ester Functions for the Brain Retention of 99mTc-Labelled Ethylene Dicysteine Diethyl Ester (99mTc-ECD)." *Nuclear Medicine and Biology*, vol. 25, No. 6, 1998, pp. 569-575.
Schibli, Roger, et al. "Influence of the Denticity of Ligand Systems on the in Vitro and in Vivo Behavior Of99mTc(I)-Tricarbonyl

(56) References Cited

OTHER PUBLICATIONS

Complexes: A Hint for the Future Functionalization of Biomolecules." *Bioconjugate Chemistry*, vol. 11, No. 3, 2000, pp. 345-351.

Neirinckx et al. "Technetium-99m d,I-HM-PAO: A New Rathopharmaceutical for SPECT Imaging of Regional Cerebral Blood Perfusion". 1987, vol. 28, 191-202.

Bussière, Thierry, et al. "Morphological Characterization of Thioflavin-S-Positive Amyloid Plaques in Transgenic Alzheimer Mice and Effect of Passive Aβ Immunotherapy on Their Clearance." *The American Journal of Pathology*, vol. 165, No. 3, 2004, pp. 987-995.

Klunk, William E., et al. "Uncharged Thioflavin-T Derivatives Bind to Amyloid-Beta Protein with High Affinity and Readily Enter the Brain." *Life Sciences*, vol. 69, No. 13, 2001, pp. 1471-1484.

Hartley, Dean M., et al. "Protofibrillar Intermediates of Amyloid β-Protein Induce Acute Electrophysiological Changes and Progressive Neurotoxicity in Cortical Neurons." *The Journal of Neuroscience*, vol. 19, No. 20, 1999, pp. 8876-8884.

Nunez, Joseph. "Primary Culture of Hippocampal Neurons from P0 Newborn Rats." *Journal of Visualized Experiments*, No. 19, 2008.

Berridge, Michael V., et al. "Tetrazolium Dyes as Tools in Cell Biology: New Insights into Their Cellular Reduction." *Biotechnology Annual Review*, 2005, pp. 127-152.

Gella, Alejandro, and Nuria Durany. "Oxidative Stress in Alzheimer Disease." *Cell Adhesion & Migration*, vol. 3, No. 1, 2009, pp. 88-93.

Cheignon, C., et al. "Oxidative Stress and the Amyloid Beta Peptide in Alzheimer's Disease." *Redox Biology*, vol. 14, 2018, pp. 450-464.

Allan Butterfield, D. "Amyloid β-Peptide (1-42)-Induced Oxidative Stress and Neurotoxicity: Implications for Neurodegeneration in Alzheimer's Disease Brain. A Review." *Free Radical Research*, vol. 36, No. 12, 2002, pp. 1307-1313.

LeBel, Carl P., et al. "Evaluation of the Probe 2',7'-Dichlorofluorescin as an Indicator of Reactive Oxygen Species Formation and Oxidative Stress." *Chemical Research in Toxicology*, vol. 5, No. 2, 1992, pp. 227-231.

\* cited by examiner

TRICARBONYL COMPLEXES OF TRANSITION METALS WITH BENZO-HETEROCYCLIC DERIVATIVES OF THE CYCLOPENTADIENYL ANION

CROSS-REFERENCE TO RELATED APPLICATIONS

This application is a 371 U.S. National Phase of International Application No. PCT/EP2019/057235, filed Mar. 22, 2019, which claims priority to Greek Patent Application No. 20180100128, filed Mar. 22, 2018. The entire disclosures of the above applications are incorporated herein by reference.

TECHNICAL FIELD

The present invention relates to appropriately designed complexes of transition metals that exhibit high permeability of the blood-brain barrier and can be used as diagnostic/therapeutic agents of CNS diseases. More specifically, it relates to a) the radiodiagnosis of widespread CNS diseases, including Alzheimer's disease and brain tumors, and b) the therapeutic application of these complexes.

BACKGROUND OF THE INVENTION

Blood-Brain Barrier and CNS Drugs

Crossing of the blood-brain barrier (BBB) is the bottleneck in the development of drugs for the Central Nervous System (CNS) and especially for the brain [1]. The blood-brain barrier is characterized by the close arrangement and tight junctions of endothelial cells in CNS capillaries, and serves to maintain the microenvironment of the brain cavity stable and to prevent the entrance of toxic agents. The protection offered by BBB creates a big obstacle to the effective transport of drugs for therapeutic intervention against brain pathologies. It is characteristic that the presence of BBB prevents >98% of all low molecular weight drugs (400-500 Da) and ~100% of the high molecular weight ones as well as of biotechnological products (monoclonal antibodies, proteins, gene therapy agents) to reach the brain. Besides the low molecular weight, a series of physicochemical characteristics affect the BBB crossing, out of which lipophilicity is the most important [2]. Out of the ~7000 small-molecule drugs reported in the Comprehensive Medicinal Chemistry database, only 5% address the CNS and treat limited type of pathologies (schizophrenia, depression, epilepsy, chronic pain). Despite the successful results of CNS drug research, the lack of effective transport of the novel therapeutics through the BBB, prevents their translation from the lab to the clinic. Consequently, and mainly due to the existence of the BBB, there exist no effective clinical therapeutic treatments for a large number of CNS disorders, including Alzheimer's disease, Huntington disease, amyotrophic lateral sclerosis (A.L.S.), brain tumors, brain and CSF injuries, bacterial infections etc. Therefore, the need for drugs that will cross the BBB is justified and big.

Alzheimer's Disease

Alzheimer's disease (AD) presents a characteristic example of an extremely widespread CNS disease for which all therapeutic approaches are limited by the presence of the BBB [3]. AD is the main form of dementia (~70% of the total cases) and mainly affects the elderly. Approximately 46 million people worldwide suffer from dementia, making it the 7th leading cause of death globally, while the number of sufferers is expected to rise dramatically in the near future due to the increase in life expectancy. One of the main histopathological features of AD is the presence of amyloid plaques in the extracellular space of the brain [4]. The main protein constituent of amyloid plaques is the 40- or 42-amino acid β-amyloid peptide. The β-amyloid peptide under conditions which are still not fully understood aggregates into insoluble fibrils which progressively accumulate to form the amyloid plaques with the participation of other agents. According to the leading theory on the AD pathogenesis (the amyloid cascade hypothesis), the aggregation of β-amyloid to fibrils and the subsequent formation of amyloid plaques are related to the pathology of AD [5, 6]. Therefore, they constitute a target for diagnostic and therapeutic approaches against AD. To date, there is no clinical laboratory examination and testing protocol able to provide early, accurate and selective diagnosis of AD. The clinical practice has established a set of diagnostic criteria which include neuropsychological, biochemical and imaging examinations aiming at distinguishing AD from other closely related disorders which present similar symptoms (such as physiological aging, vascular dementia, ischemic episodes, depression, etc.) [7, 8]. In 2012, the FDA (Food and Drug Administration, USA) approved florbetapir F-18 (commercial name: Amyvid, Scheme 1A) as the first radiodiagnostic probe for tracing the amyloid plaques of AD using Positron Emission Tomography (PET), followed by flutametamol F-18 (Visamyl, Scheme 1B) in 2013, and florbetaben F-18 in 2014 (Neuraceq, Scheme 1C) [9]. Imaging with PET is not a routine examination, but it is mostly used for confirmation in burdened clinical conditions [10]. However, the recent NIH-supported revision in Alzheimer's diagnostic guidelines focusing on early diagnosis before mental decline becomes evident, emphasizes the need for broader use of imaging modalities [11].

In parallel to the development of PET radiodiagnostics, the quest for radiodiagnostics of $^{99m}$Tc (γ-emitter) for the detection of amyloid plaques with γ-camera tomography (Single Photon Emission Computed Tomography, SPECT) has attracted scientific interest worldwide. This is due to the fact that $^{99m}$Tc, the most widely clinically used radionuclide, possesses ideal properties for in vivo imaging, it is widely and more economically available via the portable $^{99}$Mo/$^{99m}$Tc generators, without requiring a cyclotron infrastructure for its production, as PET isotopes do. A great number of $^{99m}$Tc labeled compounds of various structures (including derivatives of benzofuran, flavone, chalcone, benzothiazole, benzoxazole, curcumin, chrysamin, Congo red) and of various coordination modes have been synthesized aiming at the development of a radioagent with affinity for amyloid plaques and satisfactory BBB permeability [9, 12]. Among the various $^{99m}$Tc cores that have been employed in the quest of a $^{99m}$Tc radioagent for AD diagnosis, special mention is made of the cyclopentadienyl tricarbonyl metallic core [Cp$^{99m}$Tc(CO)$_3$], also employed in the current invention [13]. This organometallic core exhibits extremely favorable properties for the development of a CNS radiopharmaceutical, as it is characterized by low molecular weight and small size, suitable lipophilicity, stability and facile conjugation to bioactive molecules able to bind to amyloid plaques [14]. The cyclopentadienyl tricarbonyl complexes in the literature, include chalcone mimics (Scheme 2A) or 2-(4'-aminophenyl)benzothiazole conjugates joined through ester (Scheme 2B, 2C) or amide (Scheme 2D) bond [15-18]. The evaluation of the novel $^{99m}$Tc complexes aiming to act as radiodiagnostics is done through the determination of their chemical affinity for amyloid plaques (in vitro and ex vivo), the determination of their binding constant K to amyloid fibrils, and through the assessment of their brain uptake (expressed as % injected dose/g of organ, % ID/g) by means of biodistribution experiments in mice [17]. In a recent review, which summarizes the existing literature data [9], it is shown that the cyclopentadienyl tricarbonyl $^{99m}$Tc complexes exhibit moderate to high affinity for β-amyloid aggregates ($K_i$=12.4-204.1 nM) and potential to stain the amyloid plaques in vitro. However, in biodistribution experiments there is only limited brain uptake for the majority of them, with the highest being 1.06% ID/g. To date there exists no $^{99m}$Tc complex which gathers all the desired properties to enter the stage of clinical evaluation as an agent for the early diagnosis of AD.

To date there is no cure for Alzheimer's disease. The currently available treatments are only symptomatic and aim to alleviate cognitive impairment through the strengthening of neurotransmission [19]. Despite the great scientific investment, only five drugs are currently available to treat symptoms related to memory and thinking. One of the main therapeutic approaches against AD, is the inhibition of the aggregation of β-amyloid peptide either to soluble oligomers (which are also associated with neurotoxicity[20]) or to insoluble amyloid fibrils. A large number of synthetic small molecules and natural products have been studied in vitro for their interaction with the β-amyloid peptide and their potential to interfere in its aggregation process with encouraging results [21, 22]. The efficacy of the potential inhibitors in preventing the aggregation of β-amyloid peptide is evaluated with the thioflavin T (ThT) fluorescence assay, which detects amyloid fibrils, and with electron microscopy techniques [23]. It is also done through the determination of their potential to rescue neuronal cells from β-amyloid peptide cytotoxicity [24]. Although many compounds in the literature are known to interfere with the β-amyloid aggregation and many (>400) of them are in clinical trials ([25], their low BBB permeability is usually the main reason that inhibits their development into pharmaceutical agents to treat AD [3].

Brain Cancer

Brain cancer (primary and metastatic) is characterized by short survival expectancy with only 14% of the total number of patients in developed countries surviving for 10 years after the initial diagnosis. It is worth noting that although the incidence of CNS tumors worldwide is only 1.8% [26] their frequency is constantly rising among the younger ages. According to 2016 statistics, brain cancer is the most common type in children (age 0-14 years of age) and the third most frequent in the 15-39 years age group [26, 27].

Despite the fact that there are various effective anticancer drugs, their application in neuro-oncology is primarily restricted by the presence of the BBB [28]. As a result of their limited penetration through the BBB and their low concentration at the tumor site, the choices for systemic therapy are few and their impact on the survival of the patient is debatable [29, 30]. As a result, the main therapeutic strategies for brain tumors are radiotherapy and surgery with low curative rates in both cases. It is therefore clear that the effective fight of brain tumors is closely related with transport across the BBB, a prime goal for pharmaceutical research the last decade [31].

Currently, brain tumor diagnosis is based on characteristic clinical symptoms, neurological examination and brain imaging, mainly with Magnetic Resonance Imaging (MRI) [32]. Imaging with radiopharmaceuticals (PET, SPECT) is extremely important in following the progress of the disease after treatment or surgery when inflammation at the tumor site or the presence of necrotic tissue make the observation of the tumor with MRI difficult. Among the radiolabeled compounds that have been clinically used for brain tumor imaging (such as $^{121}$TlCl or $^{18}$F-FDG) a number of $^{99m}$Tc tracers, such as $^{99m}$Tc-tetrofosmin, $^{99m}$Tc-sestamibi, $^{99m}$Tc-glucoheptonate are included [33]. These drugs are not specific and their location at the tumor site is mainly due to the increased blood supply at the tumor site. Based on these facts, any $^{99m}$Tc complex which is able to successfully cross the BBB at a clinically sufficient degree—as the novel molecules which are the subject of the current invention—can result in clearer imaging and safer diagnosis. When the radioactive isotopes of rhenium, $^{186}$Re and $^{188}$Re, which afford complexes of the same structure with $^{99m}$Tc and emit β-radiation suitable for therapeutic interventions [34] serve as the metal core, the resulting complexes are strong candidates for brain tumor therapy. Finally, it is well known that a number of molecules exhibiting antitumor activity contain the benzothiazole, benzimidazole or benzoxazole pharmacophoric moiety in their structure [35-38].

SUMMARY OF THE INVENTION

The present invention provides tricarbonyl complexes of transition metals with benzo-heterocyclic derivatives of the cyclopentadienyl anion. The compounds of the present invention exhibit high permeability of the blood-brain barrier and can be used as diagnostic or therapeutic agents of CNS diseases, such as Alzheimer's disease or CNS tumors.

DETAILED DESCRIPTION OF THE INVENTION

Figure 1:
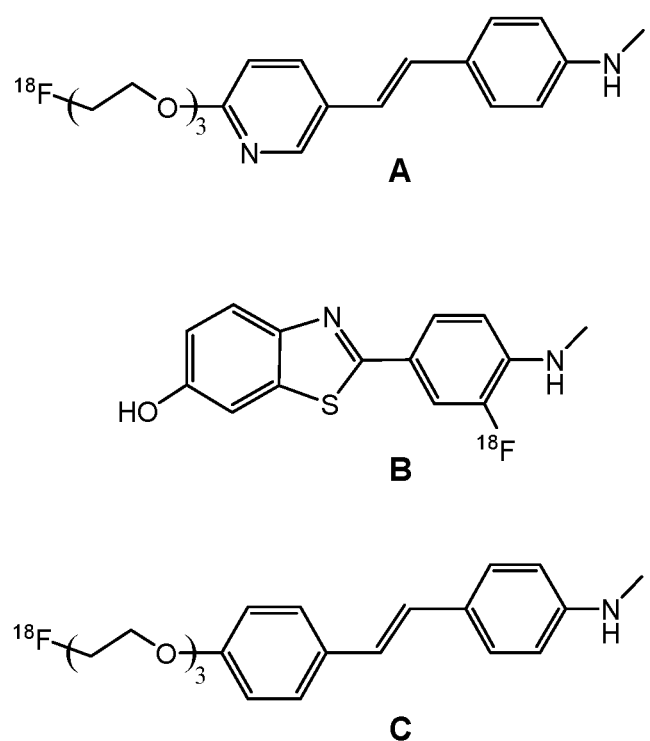
FIG. 1 presents the chemical structure of the FDA approved $^{18}$F labeled radiodiagnostic agents used for tracing the amyloid plaques of Alzheimer disease with PET.
Figure 2:
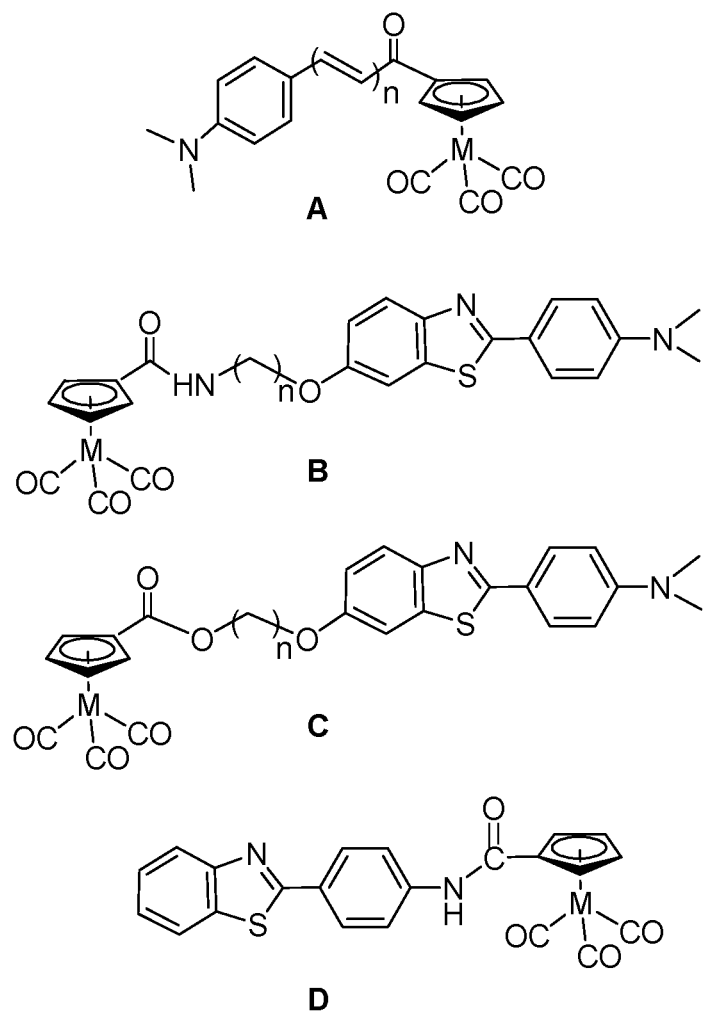
FIG. 2 presents the chemical structures of cyclopentadienyl complexes that have been reported in the literature as potential radiodiagnostics against Alzheimer's disease.
Figure 3:
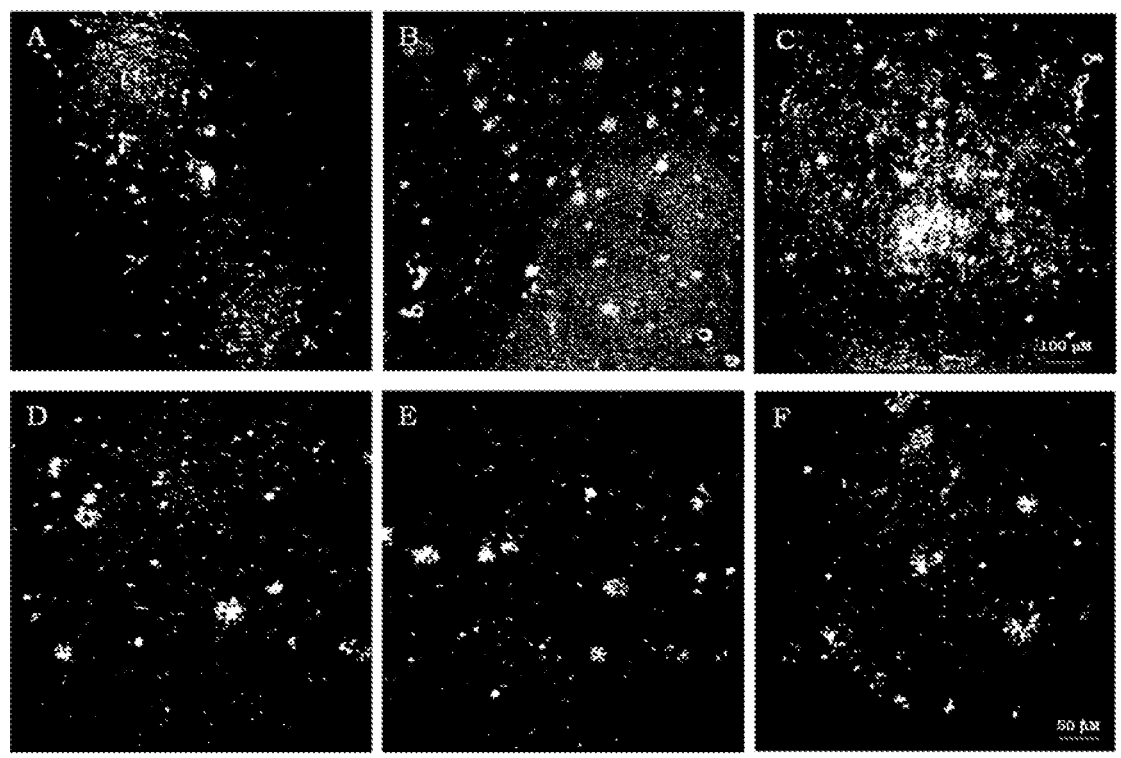
FIG. 3 presents the application of the non-radioactive Re complexes in in vitro imaging studies of amyloid plaques by means of confocal fluorescent microscopy (DAPI filter, excitation 365 nm, emission 445 nm), Example 10. More specifically, the staining with complexes Re-2 (A), Re-3 (B), Re-4 (D) και Re-5 (E) of temporal cortex brain tissue sections (6 μm thick) from an AD patient is shown. For comparison purposes, corresponding tissue sections were stained with Thioflavin S (C, F). The scale bar corresponds to 100 μm in A, B, C and 50 μm in D, E, F.

The present invention relates to the development and application of metal complexes that exhibit high blood-brain barrier (BBB) permeability and can be used as diagnostic probes or therapeutic agents for brain and CNS diseases in general. More specifically, the invention describes the use of cyclopentadienyl anion, directly bonded with small molecular weight heterocyclic moieties of the benzothiazole, benzimidazole and benzoxazole families of compounds acting as ligands of the tricarbonyl metal core $M(CO)_3^+$ and leading to the formation of complexes represented by the general structural formula 1. Thus, the present invention provides a compound of formula 1 or a pharmaceutically acceptable salt thereof

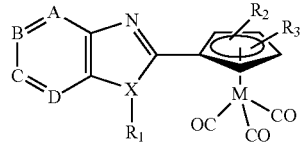

wherein

M is Re, Tc, Mn or other transition metal capable of forming a tricarbonyl cyclopentadienyl entity of the type $CpM(CO)_3^+$ X is S (benzothiazole family), N (benzimidazole family), O (benzoxazole family)

A is N or C—$R_A$, B is N or C—$R_B$, C is N or C-Rc, D is N or C—$R_D$, wherein $R_A$, $R_B$, $R_C$, $R_D$ are the same or different and are selected from hydrogen, halogen, nitro-, alkyl-, haloalkyl- with 0 to 3 halogen atoms on each carbon atom, aminoalkyl-, alkylamino-, hydroxyl, alkyloxy-, benzyloxy-, aryloxy-, —$SO_2$—C(=O)$NR_4R_5$, —C(=S)$NR_4R_5$, —$SO_2NR_4R_5$, —NC(=O)$R_4$, wherein $R_4$, $R_5$ are the same or different and are hydrogen or $C_1$-$C_6$ alkyl- $R_1$ for X=N is hydrogen, alkyl-, alkenyl-, haloalkyl- with 0 to 3 halogen atoms on each carbon atom, alkoxyalkyl-, cycloalkyl-, arylalkyl-, whereas for X=S, $OR_1$ does not exist $R_2$, $R_3$ are the same or different and are selected from hydrogen, —$NR_4R_5$, —NC(=O)$R_4$ wherein $R_4$, $R_5$ are the same or different and are hydrogen or $C_1$-$C_6$ alkyl-.

The compounds of formula 1 can be synthesized following procedures well known in the art, for example, as illustrated in Scheme 1 below. The appropriately substituted ferrocenylcarbaldehyde undergoes an oxidative cyclization with the appropriately substituted aromatic aminothiol, diamine or aminoalcohol to afford the corresponding ferrocenyl benzothiazole, benzimidazole, benzoxazole bearing the desired substitutions. Any of the latter is subsequently reacted with a metal tricarbonyl-bearing precursor complex to cause the replacement of the iron-Cp moiety by the metal tricarbonyl core and to generate the final cyclopentadienyl metal tricarbonyl benzothiazole, benzimidazole, benzoxazole.

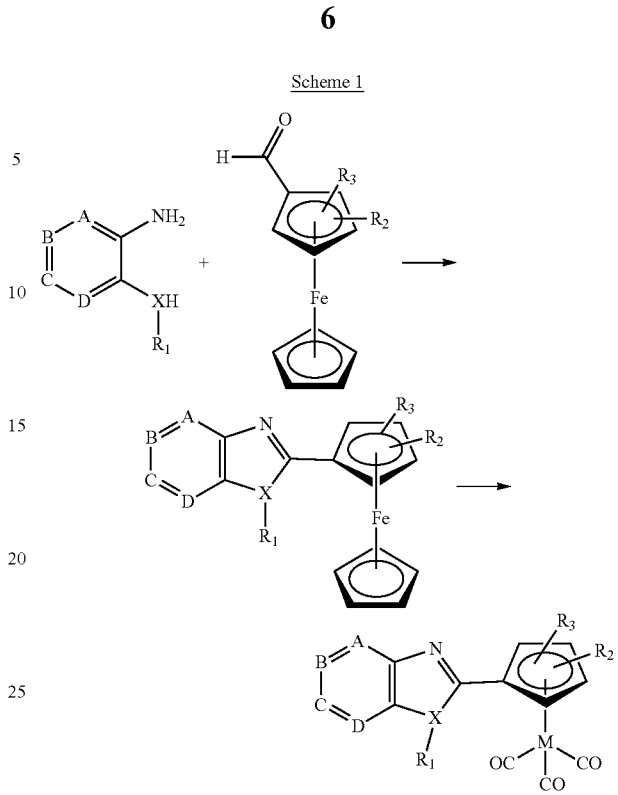

Scheme 1

The complexes of the present invention exhibit high BBB permeability (Example 9) and can be used as diagnostic or therapeutic agents of CNS diseases, such as Alzheimer's disease or CNS tumors. Namely, compounds of the general formula 1 exhibit high affinity for the amyloid plaques which characterize the pathology of AD (Example 10) and may therefore be applied as imaging/diagnostic agents through the use of the radioactive $^{99m}$Tc for SPECT diagnosis. Moreover, they show strong interactions with amyloid fibrils (Example 11), they inhibit β-amyloid peptide induced toxicity in primary neuronal cells (Example 12) and they also show antioxidant activity against reactive oxygen species (ROS), which are greatly increased in AD (Example 13). Therefore the compounds of the present invention act as therapeutic agents against AD. In addition to application in AD, the increased crossing of the BBB is an important finding for the extension of the invention towards the diagnosis and therapy of brain tumors via the uptake of compounds of the general structure 1 through the increased vasculature of a growing tumor. The diagnostic application is preferably realized through the use of the radioactive metal $^{99m}$Tc and SPECT imaging, whereas the therapeutic application is preferably realized through the use of the rhenium radioisotopes $^{186}$Re and $^{188}$Re, which emit β-radiation suitable for radiotherapy.

The greatest advantage of the compounds of the present invention is their high BBB penetration potential which for example reaches 7.04% ID/gr for compound $^{99m}$Tc-2 (Example 9). This penetration is significantly higher than any other reported for $^{99m}$Tc complexes designed as potential radiodiagnostic agents for AD, the best of which reaches 1.21% ID/gr at 2 min post administration [9] and it is comparable to the penetration of the clinically used radiodiagnostic agents for brain perfusion, such as $^{99m}$Tc-HM-PAO (5% ID/gr in 60 min post administration [39]) and $^{99m}$Tc-ECD (1.32% ID/organ in 2 min post administration [40], approximately 4.4% ID/gr). The prime importance of the brain for life in combination with the difficulty of reaching the closed cranioencephalic cavity due to the existence of the BBB, accentuates the importance of the present invention, especially when considering the few available drugs for therapeutic interventions against brain diseases.

When the compounds of the present invention are used in the form of a pharmaceutically acceptable salt, such salts can be prepared for example by combining the compounds with an appropriate pharmaceutically acceptable acid or base. Such acids or bases are well known in the art.

The compounds of the present invention are preferably administered in the form of a pharmaceutical or diagnostic composition. Such compositions are well known to a person skilled in the art. For diagnostic applications a radiolabeled compound of the present invention is preferably administered intravenously as an aqueous physiologic saline solution. The radioactivity of the injected dose (usually ranging between 5-15 mCi) is adjusted to allow the imaging of amyloid plaques or brain tumors or other lesions of interest with SPECT.

For therapeutic applications a compound of the present invention is preferably combined with one or more excipients to form a pharmaceutical composition. Depending on the mode of administration and the form of the composition, the one or more excipients are preferably selected from the group consisting of: pH adjusters, osmotic agents, emulsifiers, dispersing agents, surfactants, solubilizers, buffering agents, preservatives, wetting agents, gelling agents, consistency agents, chelating agents, suspending agents, thickening agents, or combinations thereof. In the case where a radioactive $^{188}$Re or $^{186}$Re compound is applied for the radiotherapy of brain tumors or other lesions, the compound is preferably administered intravenously as an aqueous physiologic saline solution and at the therapeutically effective radioactivity dose.

EXAMPLES

Towards the implementation of the present invention, the following Examples with experimental results are presented:
Synthesis of the precursor molecules Fe-2-Fe-6 (Examples 1-5)
Synthesis of the desired complexes with stable (non-radioactive) Re (Re-2-Re-6, Example 6)
Synthesis of the desired complexes with radioactive $^{99m}$Tc ($^{99m}$Tc-2-$^{99m}$Tc-5, Example 7)
Evaluation of the stability and lipophilicity of $^{99m}$Tc-2-$^{99m}$Tc-4 (Example 8)
Evaluation of blood-brain barrier penetration with biodistribution experiments with mice (Example 9)
Application of the complexes in Alzheimer's disease relevant challenges including staining of the amyloid plaques in brain tissue with complexes Re-2-Re-5 (Example 10), determination of the affinity constant for binding of complexes
$^{99m}$Tc-2-$^{99m}$Tc-4 to amyloid fibrils (Example 11), inhibition of the toxicity induced by amyloid fibrils in primary neuronal cells with complexes Re-2, Re-3 (Example 12) and determination of the antioxidant activity against ROS for complexes Re-2, Re-3 (Example 13).
It has to be noted that Re and $^{99m}$Tc metals have very similar physical and chemical properties and they form complexes with comparable biological behavior. Herein, the non-radioactive Re metal is used in place of the radioactive $^{99m}$Tc for the purposes of synthesis, isolation and characterization of the compounds (Example 6) as well as in many biological evaluation procedures for practical reasons, to ease the experimental requirements and to reduce unnecessary exposure to radioactivity (Examples 10, 12, 13), whereas $^{99m}$Tc is irreplaceable for the biodistribution experiments in experimental animals (Example 9).

Example 1

Synthesis of ferrocenyl-benzothiazole (Fe-2)

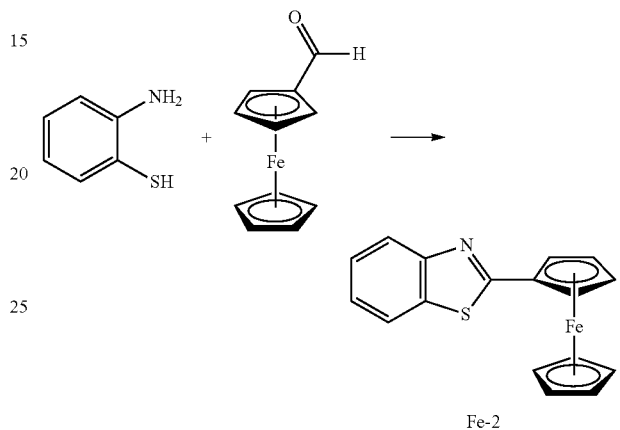

Fe-2

A mixture of ferrocenecarboxaldehyde (1.1 g, 5 mmol) and 2-aminothiophenol (600 µL, 5.6 mmol, 1.1 eq) in ethanol (40 mL) was stirred under reflux for 16 hours. The reaction was returned to r.t and precipitation of a brown-red solid occurred. The final product was obtained by flash column chromatography of the precipitate eluting with hexane:ethyl acetate (98:2 to 96:4). Yield: 92%. NMR (DMSO-$d_6$, ppm): $^1$H (500 MHz) 8.03, 7.92, 7.47, 7.39, 5.02, 4.60, 4.16; $^{13}$C (126 MHz) 153.43, 126.24, 124.52, 121.96, 121.80, 70.82, 70.13, 68.50. MS (ESI) m/z: [M+H]$^+$ calculated $C_{17}H_{14}NS^{56}Fe$, 320.0188; found, 320.0188.

Example 2

Synthesis of ferrocenyl-benzimidazole (Fe-3)

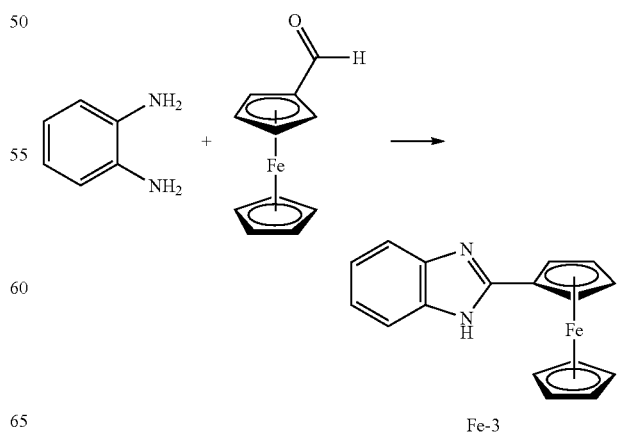

Fe-3

A mixture of ferrocenecarbaldehyde (0.76 g, 4 mmol) and sodium bisulfite (1.44 g, 1.4 mmol) were dissolved in 20 mL of a mixture of absolute ethanol and water (1:1). The reaction mixture was refluxed for 1 hour. o-Phenylenediamine (0.4 g, 4 mmol) was added at room temperature and the mixture was refluxed for an additional 1 hour. It was then cooled to room temperature and eventually refrigerated. The precipitate formed was filtrated, then washed successively with ice cold water and cold absolute ethanol. The pure product was isolated by flash column chromatography of the precipitate eluting with dichloromethane:ethyl acetate (96:4). Yield: 62%. NMR (DMSO-$d_6$, ppm): $^1$H (500 MHz) 12.35, 7.54, 7.44, 7.13, 5.04, 4.47, 4.10; $^{13}$C NMR (126 MHz) 152.92, 120.86, 117.50, 110.15, 69.31, 68.91, 66.90.

Example 3

Synthesis of ferrocenyl-N-methyl-benzimidazole (Fe-4)

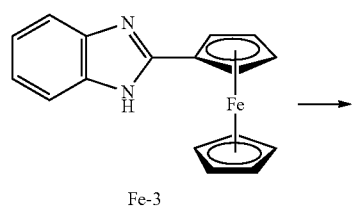

Fe-3

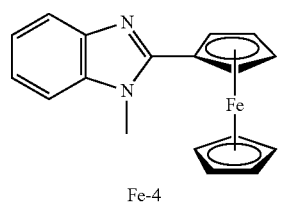

Fe-4

In a solution of NaOH (0.535 g, 13.4 mmol) in water (1 mL) a solution of acetone (7.5 mL) and ferrocenyl-benzimidazole (Fe-3) (0.54 g, 1.8 mmol) was added and stirred for 5 minutes, followed by the dropwise addition of methyliodide (145 μL, 2.3 mmol) at 0° C. The reaction mixture was stirred for 1 h at r.t, then acetone was evaporated under vacuum and the mixture was diluted with water (50 mL) and it was consequently extracted with dichloromethane (3×30 mL). The combined organic phases were washed with brine, dried with $Na_2SO_4$ and the solvent was evaporated in vacuo to yield a light brown oily product. The pure product was afforded by means of flash column chromatography eluting with dichloromethane:ethyl acetate (96:4). Yield: 95%. NMR (DMSO-$d_6$, ppm): $^1$H (500 MHz) 7.55, 7.22, 7.17, 4.99, 4.53, 4.21, 4.03; $^{13}$C NMR (126 MHz) 152.74, 142.57, 136.71, 121.51, 118.04, 69.80, 69.25, 68.77, 31.19.

Example 4

Synthesis of ferrocenyl-benzoxazole (Fe-5)

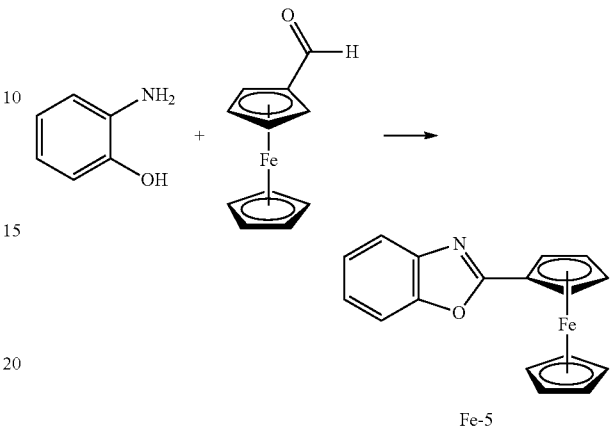

Fe-5

The mixture of ferrocenecarboxaldehyde (642 mg, 3.00 mmol) and 2-aminophenol (330 mg, 3.00 mmol) was stirred at r.t. in 5 mL acetic acid for 15 min. This was followed by the dropwise addition of 20 mL hot acetic acid solution of PbAc$_4$ (1350 mg, 3.03 mmol) into the system in 30 min, and the mixture was then poured onto 50 g ice. The aqueous phase was extracted with dichloromethane (3×30 mL), and the combined organic phase was washed with brine, dried with $Na_2SO_4$ and the solvent was removed under vacuum. The remaining solid was purified by means of flash column chromatography eluted by dichloromethane:hexane (10:90). Yield: 42%. NMR (DMSO-$d_6$, ppm): $^1$H (500 MHz) 7.69, 7.35, 5.06, 4.62, 4.20; $^{13}$C (126 MHz) 165.53, 150.00, 141.86, 124.46, 124.34, 118.83, 110.47, 71.10, 69.62, 68.24.

Example 5

Synthesis of 2-dimethylaminoferrocene-benzothiazole (Fe-6)

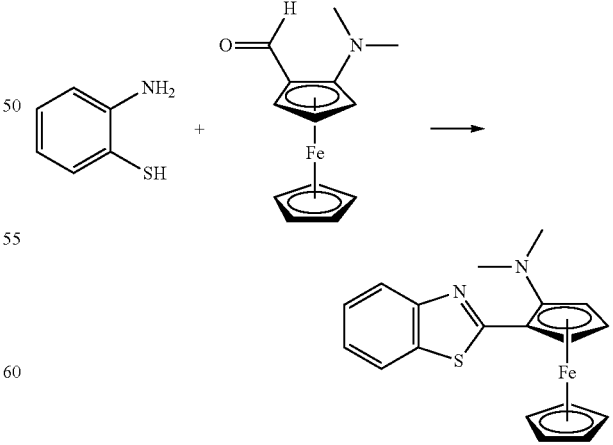

Fe-6

The synthetic protocol is the same as in Example 1 using 2-aminothiophenol and 2-dimethylaminoferrocenecarboxaldehyde. The pure product is afforded by flash column chromatography with dichloromethane:ethyl acetate (96:4). Yield: 53%. NMR (DMSO-d$_6$, ppm): $^1$H (500 MHz) 8.04, 7.93, 7.47, 7.40, 4.97, 4.58, 4.51, 4.11, 2.16; $^{13}$C (126 MHz) 153.02, 126.11, 124.49, 121.85, 121.71, 97.5, 73.64, 70.64, 69.81, 69.09, 44.69.

The 2-dimethylaminoferrocenecarboxaldehyde was prepared from ferrocene carboxylic acid according to the following synthetic scheme:

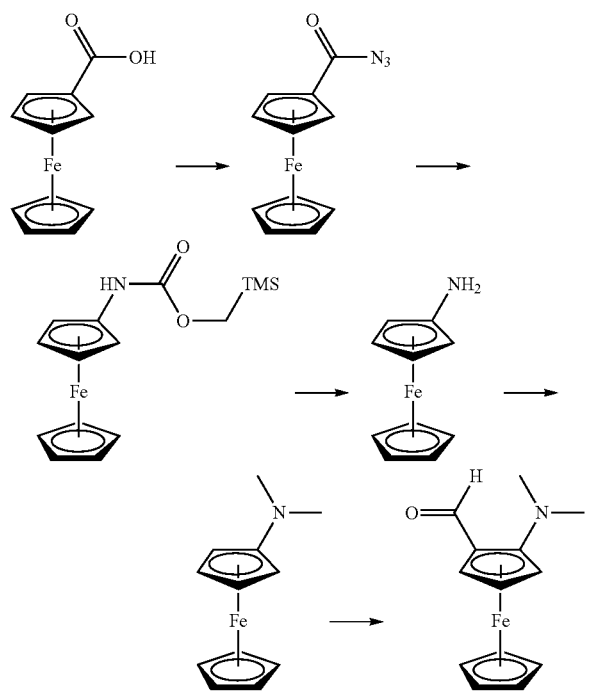

A solution of ferrocene carboxylic acid (2.3 g, 10 mmol) in dry dichloromethane (20 mL) was treated with oxalyl chloride dropwise (1.8 mL, 20 mmol) at 0° C. under nitrogen with the addition of four drops of DMF. The reaction mixture was returned to r.t. and stirred for 3 hours. The solvent and the excess oxalyl chloride was removed under nitrogen, and the resulting red solid was redissolved to fresh dry dichloromethane (20 mL). Tetrabutylammoniun bromide (12 mg, 0.03 mmol) was added followed by the addition of a NaN$_3$ solution (1 g, 15 mmol) in water (5 mL). The reaction mixture was stirred under nitrogen and at r.t for a further 18 h. The reaction was quenched by the addition of water (50 mL) and the organic phase was separated, and the aqueous was further extracted with dichloromethane (2×20 mL). The combined organic phase was washed with brine, dried with Na$_2$SO$_4$ and the solvent was removed under vacuum. The desired azide was isolated by flash column chromatography eluting with dichloromethane:hexane (1:1). Yield: 78%. NMR (CDCl$_3$, ppm): $^1$H (500 MHz) 4.78, 4.55, 4.05; $^{13}$C (126 MHz) 176.1, 89.0, 76.3, 78.0, 80.1.

The resulting azide (2.3 mmol) was dissolved in toluene (15 mL) and heated to reflux under nitrogen (105° C.) when 2-(trimethylsilyl)ethanol (4.7 mmol) was added in one dose. The reaction solution was stirred under reflux for 3 h, and until the colour of the azide turned to orange. The reaction mixture was returned to r.t. and after the addition of NaOH solution (1 M, 50 mL) was stirred for a further 10 minute. The organic phase was separated and the aqueous was extracted further with dichloromethane (2×20 mL). The combined organic phase was washed with brine, dried with Na$_2$SO$_4$ and the solvent was removed under vacuum resulting in the formation of a reddish solid, which afforded the pure product by recrystallization dichloromethane/hexane.

The so formed carbamide (2.1 mmol) was dissolved in 1 M TBAF in THF and the reaction mixture was warmed to 50° C. for 15 min. The solvent was removed under vacuum and dichloromethane (50 mL) and water (50 mL) was added. The two phases were separated and the aqueous phase was extracted further with dichloromethane (2×20 mL). The combined organic phase was washed with brine, dried with Na$_2$SO$_4$ and the solvent was removed under vacuum affording the amino-ferrocene as a reddish solid. NMR (CDCl$_3$, ppm): $^1$H (500 MHz) 4.09, 4.00, 3.85, 260; $^{13}$C (126 MHz) 105.63, 68.85, 63.43, 58.80.

This amino-ferrocene (1.07 g, 5.32 mmol) was dissolved in acetic acid (15 mL) under nitrogen and paraformaldehyde (1.59 g, 53.2 mmol) and NaBH$_3$CN (1.67 g, 26.6 mmol) was added and the reaction mixture was stirred for 16 h. Aqueous NaOH 6 M was added until pH=12 and the solution was extracted by hexane (3×20 mL). The combined organic phase was washed with brine, dried with Na$_2$SO$_4$ and the solvent was removed under vacuum until approximately 5% of the initial volume. The residue was subjected to quick filtration through a pad of silica gel eluting with hexane. The solvent was removed under vacuum not to complete dryness so as the pure product crystallized in the freezer as orange flakes; mp 69-70° C.; NMR (CDCl$_3$, ppm): $^1$H (500 MHz) 4.25, 3.95, 3.76, 2.59; $^{13}$C (126 MHz) 155.80, 66.50, 63.07, 54.61, 41.50.

A solution of dimethylamino-ferrocene (0.229 g, 1 mmol) in THF (0.1 M) at 0° C. and under nitrogen was treated with BF$_3$·OEt$_2$ (1.05 eq). The reaction solution was stirred and it was then cooled to −78° C. in an acetone-dry ice bath, followed by the addition of n-BuLi (1.10 equiv., in hexane) and the temperature was allowed to reach −40° C. Within one hour the color changed from yellow to orange-red and then the temperature was returned to −78° C., when DMF (1.20 eq) was added and the reaction was allowed to return slowly to r.t. The reaction was quenched by the careful addition of hexane and saturated NaHCO$_3$. The two phases were separated and the aqueous phase was extracted further with ether (2×20 mL). The combined organic phase was washed with brine, dried with Na$_2$SO$_4$ and the solvent was removed under vacuum. The pure product was isolated by means of flash column chromatography eluting with hexane/Et$_2$O/Et$_3$N 94:5:1. NMR (CDCl$_3$, ppm): $^1$H (500 MHz) 10.13, 4.63, 4.40, 4.29, 4.27, 2.70; $^{13}$C (126 MHz) 192.81, 117.53, 71.81, 69.52, 67.71, 66.23, 60.22, 45.61

Example 6

Synthesis of the Cyclopentadienyl Complexes with Tricarbonyl Rhenium (Re-2-Re-6)

The ferrocenyl compounds Fe-2-Fe-6 which were prepared in Examples 1-5, were converted to the respective tricarbonyl rhenium complexes Re-2-Re-6 represented by the structures

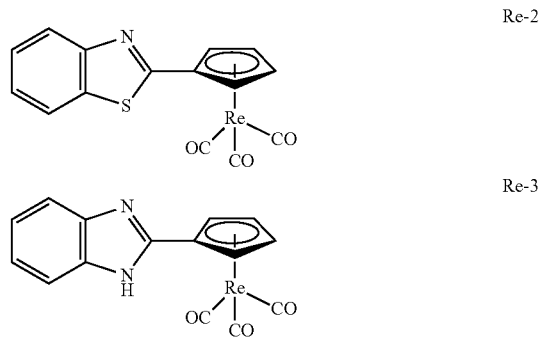

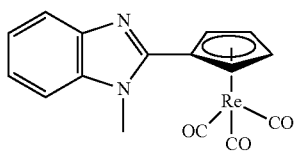

Re-4

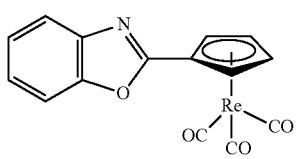

Re-5

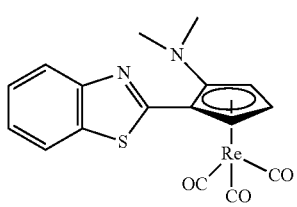

Re-6 according to the general protocol described for compound Re-2:

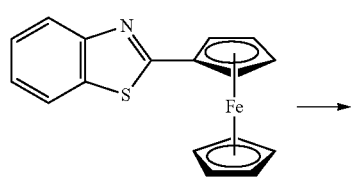

Fe-2

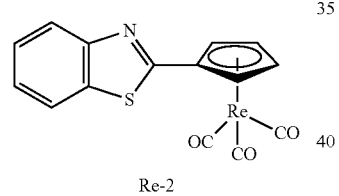

Re-2

In a solution of the precursor complex [Re(CO)$_3$Br$_3$][NEt$_4$]$_2$ (30 mg, 0.047 mmol) and the ferrocenyl derivative Fe-2 (0.098 mmol) in DMF (2.5 mL) an aqueous solution 0.1N HCl (1.8 mL) was added in a glass autoclave vial of 5 mL capacity. After a 5 minute degassing, the reaction mixture was stirred at 160° C. for 2 h. The reaction was removed for the heat, left to return to r.t. and it was then diluted with dichloromethane (10 mL). The organic phase was washed with water (3×10 mL), brine, dried with Na$_2$SO$_4$ and the solvent was removed under vacuum. The pure product Re-2 was afforded after flash column chromatography eluting with dichloromethane:ethyl acetate or hexane:ethyl acetate. NMR (DMSO-d$_6$, ppm): Re-2 $^1$H (500 MHz) 8.11, 7.98, 7.53, 7.46, 6.65, 5.88; $^{13}$C (126 MHz) 193.94, 161.06, 152.64, 134.23, 126.86, 125.83, 122.63, 122.48, 96.52, 87.09, 86.65; Re-3 $^1$H (500 MHz) 12.79, 7.56, 7.20, 6.50, 5.85; $^{13}$C NMR (126 MHz) 194.31, 145.49, 143.11, 134.23, 122.81, 121.83, 118.68, 111.18, 94.96, 86.19, 85.14; Re-4 $^1$H (500 MHz) 7.61, 7.28, 7.23, 6.54, 5.90, 3.88; $^{13}$C NMR (126 MHz) 194.22, 145.88, 141.80, 136.49, 122.83, 122.30, 118.88, 110.41, 93.94, 87.41, 86.37, 31.50; Re-5 $^1$H (500 MHz) 7.37, 7.31, 6.62, 6.60; $^{13}$C NMR (126 MHz) 194.22, 150.1, 141.21, 137.19, 125.41, 124.23, 119.90, 110.80, 94.93, 87.35, 86.30; Re-6 NMR (DMSO-d$_6$, ppm): $^1$H (500 MHz) 8.14, 7.98, 7.53, 7.48, 6.60, 6.45, 5.82, 2.32; $^{13}$C (126 MHz) 194.22, 156.02, 128.11, 126.49, 125.83, 123.71, 93.54, 72.64, 70.64, 69.79, 44.69. MS (ESI) m/z: Re-2 [M+H]$^+$ calcd for C$_{16}$H$_9$NO$_3$S$^{187}$Re, 469.9861; found, 469.9852.; Re-3 [M+H] calcd for C$_{16}$H$_{10}$N$_2$O$_3$$^{187}$Re, 453.0169, found, 453.0246.

Example 7

Synthesis of the Cyclopentadienyl Complexes with Tricarbonyl $^{99m}$Tc ($^{99m}$Tc-2-$^{99m}$Tc-5)

The ferrocenyl compounds Fe-2-Fe-5 which were prepared in Examples 1-4, were respectively converted to tricarbonyl $^{99m}$Tc complexes $^{99m}$Tc-2-$^{99m}$Tc-5, represented by the structures:

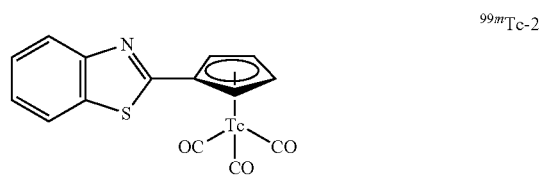

$^{99m}$Tc-2

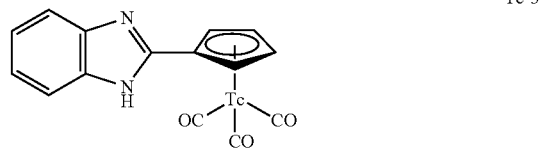

$^{99m}$Tc-3

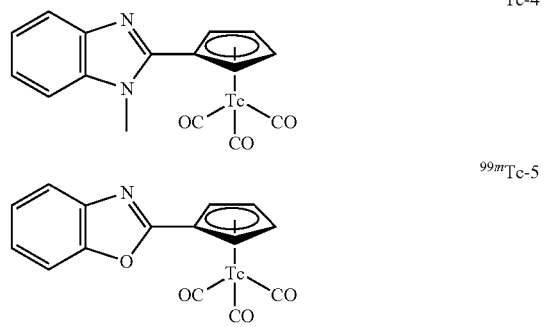

$^{99m}$Tc-4

$^{99m}$Tc-5 according to the general protocol described for compound $^{99m}$Tc-2:

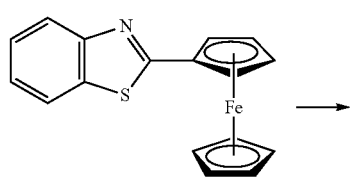

Fe-2

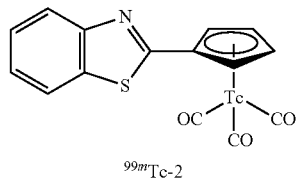

$^{99m}$Tc-2

A' method: The corresponding ferrocene precursor Fe-2 (1.0 mg) in 0.5 mL of DMF was added to the fac-$[^{99m}Tc(H_2O)_3(CO)_3]^+$ complex (0.1 mL, 180 MBq). Subsequent heating in an oil bath, under nitrogen flow, at 120° C. for 3 h afforded the corresponding $^{99m}Tc$ complex with radiochemical yield of 50% as shown by HPLC.

B' method: The corresponding ferrocene precursor Fe-2 (1.0 mg) and complex $Mn(CO)_5Br$ (1.0 mg) were dissolved in DMF (0.5 mL) and an $^{99m}TcO_4^-$ (0.1 mL, 180 MBq) aqueous solution was added. The vial was sealed and purged with nitrogen for 10 min and heated in an oil bath at 110° C. for 1 h to afford the corresponding $^{99m}Tc$ complex with radiochemical yield of 96% as shown by HPLC. In both methods, the identity of each $^{99m}Tc$ complexes was established by comparative HPLC using the analogous Re complexes as a reference. Separations were achieved on a C-18 reverse phase column (25.4×0.4 cm, 5 μm) eluted with a binary gradient system at a 1 mL/min flow rate. Mobile phase A was methanol containing 0.1% trifluoroacetic acid, while mobile phase B was water containing 0.1% trifluoroacetic acid.

Example 8

Stability and Lipophilicity of $^{99m}Tc$ Complexes

The stability of $^{99m}Tc$-2-$^{99m}Tc$-4 complexes was assessed in the presence of excess histidine and cysteine which are capable of acting as tridentate substituents replacing the ligands of the complexes [41]. Each of the HPLC-purified $^{99m}Tc$ complex (0.5 mL, approx. 10 MBq) was mixed with a solution of histidine or cysteine (2 mM) in 0.1 M PBS, pH 7.4 (0.5 mL). The mixture was incubated at 37° C. and analyzed by HPLC after 1, 3, and 6 h. The recording of the percentage of the intact complexes in the presence of the antagonists at each time point of the study allows the estimation of the stability of the labeled $^{99m}Tc$ complexes.

The lipophilicity of $^{99m}Tc$-2-$^{99m}Tc$-4 complexes was determined by the estimation of the partition coefficient in a biphasic system of n-octanol and water (PBS) [42]. The partition coefficient was expressed as the logarithm of the ratio of the counts per gram from n-octanol versus those from PBS (log $P_{oct/water}$), where P is the ratio. The measurement was done in triplicate and repeated three times.

$$P = \frac{\text{Counts}_{n\text{-octanol}}}{\text{Counts}_{PBS}}$$

The stability and lipophilicity values for $^{99m}Tc$-2-$^{99m}Tc$-4 complexes are given in Table 1.

Example 9

Estimation of Blood-Brain Barrier Permeability of $^{99m}Tc$-2-$^{99m}Tc$-4 Complexes This evaluation was conducted through biodistribution studies in healthy Swiss Albino mice (5 weeks old, 20-30 g) that were obtained from the breeding facilities of the Institute of Biosciences & Applications, NCSR "Demokritos". During these experiments we evaluate the distribution of radioactivity in the tissues of the animal after radiolabeled compound administration. For the credibility of the in vivo distribution data, three independent experiments are required for each evaluation, where in each experiment the animal population ranges between 9 and 12. The experiments of synthesis, labelling and biodistribution were carried out in the Laboratory of "Radiopharmaceuticals", NCSR "Demokritos" that has the required infrastructure to ensure safe conduct of experiments using radioactivity. All the biodistribution studies were carried out in compliance with the Presidential Decree 56/2013 (published in the Official Government Gazette of Greece 106 A/30-4-2013) that has transposed the EU Directive 2010/63 on the protection of animals used for scientific purposes.

Three groups of mice (three animals per group) were injected in the tail vein with HPLC-purified $^{99m}Tc$ complexes (1-2 μCi in 0.1 mL, ethanol/saline 1:9). The mice were sacrificed at various time points (2, 15, 90 min) post injection (p.i.). The organs of interest were excised, weighed, and the radioactivity counted in an automatic γ-counter. The stomach and intestines were not emptied of food contents prior to radioactivity measurements. The calculation for blood and muscle was based upon measured activity, sample weight, and body composition data, considering that blood comprises 7% and muscle 43% of body weight. The percentage of injected dose per organ (% ID/organ) was calculated by comparison of sample radioactivity to standard solutions that contained 10% of the injected dose. The percentage of injected dose per gram (% ID/g) was calculated by dividing the % ID/organ by the weight of the organ or tissue.

$$\% \text{ injected dose/organ} (\% \text{ ID/organ}) = \frac{(cpm \text{ organ})}{(cpm \text{ reference})}$$

$$\% \text{ injected dose/gr} (\% \text{ ID/gr}) = \frac{(cpm \text{ organ})}{(cpm \text{ reference} \times \text{organ weight})}$$

where cpm reference=(cpm 10% standard×10)−cpm tail.

The results of the biodistribution in Swiss Albino mice are given in Table 2 and 3 for $^{99m}Tc$-2 and $^{99m}Tc$-3 complexes,

TABLE 1

Stability (under the excess of histidine and cysteine) and lipophilicity (logP$_{oct/water}$) studies of $^{99m}Tc$ complexes at 37° C.

| | Stability | | | | | | Lipophilicity |
|---|---|---|---|---|---|---|---|
| | Histidine | | | Cysteine | | | |
| | 1 h | 3 h | 6 h | 1 h | 3 h | 6 h | logP$_{oct/water}$ |
| $^{99m}Tc$-2 | 98 ± 1 | 97 ± 1 | 97 ± 1 | 98 ± 1 | 97 ± 2 | 97 ± 1 | 2.52 ± 0.14 |
| $^{99m}Tc$-3 | 98 ± 1 | 98 ± 1 | 97 ± 1 | 98 ± 1 | 98 ± 1 | 97 ± 2 | 1.84 ± 0.17 |
| $^{99m}Tc$-4 | 98 ± 1 | 96 ± 1 | 95 ± 1 | 98 ± 1 | 95 ± 2 | 85 ± 1 | 1.50 ± 0.12 | where it is noticeable the outstanding percentage of radioactivity in the brain, 7.04±0.81% ID/g for $^{99m}$Tc-2 and 3.99±0.60% ID/g for $^{99m}$Tc-3. For $^{99m}$Tc-4, corresponding experiments showed an equally impressive percentage of 6.14±1.00% ID/g at 2 min.

TABLE 2

Biodistribution of radioactivity (% ID/gr) after injection of complex $^{99m}$Tc-2 in healthy Swiss Albino mice
% ID/gr

| organ | 2 min | 15 min | 90 min |
|---|---|---|---|
| Blood | 2.68 ± 0.15 | 1.06 ± 0.25 | 0.56 ± 0.04 |
| Liver | 13.33 ± 3.88 | 24.98 ± 1.23 | 28.74 ± 2.13 |
| Heart | 18.13 ± 2.33 | 2.65 ± 0.42 | 0.75 ± 0.00 |
| Kidneys | 11.65 ± 0.67 | 4.99 ± 0.90 | 4.79 ± 0.71 |
| Stomach | 1.25 ± 0.26 | 1.77 ± 1.10 | 1.74 ± 0.25 |
| Intestines | 2.76 ± 0.72 | 12.62 ± 0.80 | 20.60 ± 1.41 |
| Spleen | 2.95 ± 0.74 | 1.14 ± 0.22 | 0.55 ± 0.10 |
| Muscle | 6.70 ± 0.30 | 2.08 ± 0.07 | 0.57 ± 0.09 |
| Lungs | 14.48 ± 2.24 | 7.15 ± 1.14 | 5.18 ± 0.42 |
| Pancreas | 6.32 ± 0.59 | 2.16 ± 0.55 | 1.92 ± 1.09 |
| Brain | 7.04 ± 0.81 | 1.74 ± 0.48 | 0.32 ± 0.06 |

TABLE 3

Biodistribution of radioactivity (% ID/gr) after injection of complex $^{99m}$Tc-3 in healthy Swiss Albino mice
% ID/gr

| organ | 2 min | 15 min | 90 min |
|---|---|---|---|
| Blood | 3.38 ± 0.67 | 1.86 ± 0.13 | 0.48 ± 0.12 |
| Liver | 13.97 ± 2.13 | 30.66 ± 3.96 | 18.08 ± 1.34 |
| Heart | 7.53 ± 1.28 | 1.95 ± 0.26 | 0.22 ± 0.05 |
| Kidneys | 9.70 ± 0.92 | 5.04 ± 0.53 | 1.57 ± 0.20 |
| Stomach | 1.63 ± 0.44 | 3.17 ± 0.43 | 4.63 ± 0.56 |
| Intestines | 3.06 ± 0.08 | 14.80 ± 0.25 | 23.94 ± 4.27 |
| Spleen | 2.63 ± 0.40 | 1.01 ± 0.09 | 0.17 ± 0.03 |
| Muscle | 5.23 ± 0.79 | 1.50 ± 0.19 | 0.15 ± 0.03 |
| Lungs | 7.09 ± 0.38 | 2.44 ± 0.39 | 0.45 ± 0.13 |
| Pancreas | 5.99 ± 0.62 | 1.96 ± 0.25 | 0.21 ± 0.02 |
| Brain | 3.99 ± 0.60 | 0.75 ± 0.11 | 0.04 ± 0.01 |

Example 10

Staining of Amyloid Plaques in Post Mortem Brain Sections of Patients with Alzheimer Disease with Re-2-Re-5 Complexes Deparaffinization of AD patient sections (6 μm thick) from temporal cortex mounted on albumin-coated glass slides was carried out (xylene, 2×5 min) prior to rehydration (soaked for 5 min in 100%, 80%, 60%, then 0% ethanol-water v/v), and then incubated in phosphate buffer solution (PBS; 1.3 m NaCl, 27 mm KCl, 81 mm Na$_2$HPO$_4$, 14.7 mm KH$_2$PO$_4$, pH 7) for 30 min. The tissue preparations were treated with Re complexes as well as Thioflavin S (Th-S, for confirmation of Aβ plaques localization) solutions in dimethyl sulfoxide (DMSO) and in PBS respectively (approximately 1 mg·mL$^{-1}$) for 1 h [43]. The sections were finally washed with 40% ethanol for 2 min, followed by rinsing with tap water for 30 s and observation was performed using fluorescence confocal microscopy. Indicative microscopy images are given in Scheme 3 where it is apparent that complexes Re-2-Re-5 specifically labeled amyloid plaques in a way similar to the clinically used dye Thioflavin S.

Example 11

Binding Studies of $^{99m}$Tc-2-$^{99m}$Tc-4 Complexes Using Aβ42 Fibrillar Aggregates Amyloid peptide Aβ42 solution (final concentration of 50 μM in PBS) was incubated for 15 d at 33° C. without stirring, conditions that lead to formation of fibrillar aggregates as shown by spectrophotometric and microscopy techniques. Competitive binding assay studies were performed in 1 mL solutions in PBS in 12 mm×75 mm borosilicate glass tubes according to a published procedure with modifications. Each 1 mL solution contained proper volumes of a stock solution of Re complexes (to yield a concentration between 10$^{-4}$-10$^{-10}$ M), 50 nM of Aβ42 fibrillar aggregates and 0.2 μCi of the corresponding $^{99m}$Tc complexes. The solutions were incubated for 3 h at room temperature and the bound and free radioactivity were separated by Millex-GV Syringe Filter Unit, 0.22 μm filters followed by 2×2 mL washes with PBS at room temperature. Filters containing the bound $^{99m}$Tc complexes were measured for radioactivity in a γ-counter. Binding studies were repeated in triplicate. The data were analyzed using GraphPad Prism software with the IC$_{50}$ value calculated using a one-site competitive binding linear regression. The Ki value was calculated using the Cheng-Prousoff equation [44]:

$$K_i = \frac{IC_{50}}{(1 + [Radioligand]/K_d)}$$

where IC$_{50}$ value represents the concentration of the inhibitor (Re complex) that requires to inhibit the 50% of binding with radiolabeled $^{99m}$Tc complex, [Radioligand] and K$_d$ values are the concentration and dissociation constant respectively of the radiolabeled $^{99m}$Tc complex.

In the case of homologous competitive binding we assume that the hot and cold ligand have identical affinities so that K$_d$ and K$_i$ have the same value. Thus the above equation is being transformed into:

$$K_i = IC_{50} - [Radioligand]$$

The K$_i$ values calculated from the competitive inhibition data were 112.32±12.05 nM, 7.04±2.85 nM Kai 5.74±2.90 nM for complexes $^{99m}$Tc-2, $^{99m}$Tc-3, and $^{99m}$Tc-4 respectively. These values showed high binding affinity of Re complexes to Aβ aggregates comparable to the one of [$^{123}$I]IMPY (12.5±2.8 nM), the only SPECT Aβ imaging agent in preclinical trial [45].

Example 12

Inhibition of β-Amyloid Peptide Toxicity in Primary Neuronal Cells in the Presence of Re-2 and Re-3 Complexes Aggregation of β-amyloid peptide (Aβ) either in soluble oligomers or in insoluble fibrils is associated with the pathogenesis of Alzheimer's disease and its toxicity has been established in systemic in vitro studies employing neuronal cell cultures [46]. The evaluation of inhibition ability of Aβ42 toxicity was performed in primary hippocampal neuronal cells in the presence of Re-2 and Re-3 complexes. Hippocampal neuronal cultures were obtained from postnatal day 0-3 (P0-3) mice which are euthanized and their hippocampi were isolated, according to published protocols [47]. In particular, after being dissected, each hippocampus was enzymatically digested with 0.25% trypsin for 20 min at 37° C. The hippocampi were then rinsed in 10 ml of Hibernate-A medium containing 10% (v/v) heat-inactivated fetal bovine serum (FBS) to remove any traces of serum. After proper trituration, the cells were seeded on poly-D-lysine 96-well plates at a density of $2 \times 10^4$ per well. Cultures were maintained in Neurobasal-A medium containing 2% B-27 supplement, 0.5 mM Gluta-MAX and 1% penicillin/streptomycin at 37° C. and 5% $CO_2$, until proper differentiation. Half of the medium was replaced twice a week. After seven days of incubation in culture well plates, the primary hippocampal neurons were used for the cell viability measurements.

Solutions of Aβ42 (10 μM) in PBS in the absence or presence of the Re-2 and Re-3 complexes (1:1 and 1:2 ratio of Aβ:complexes) preincubated for 1 day at 37° C. were diluted with fresh medium and added to individual wells at a final concentration of Aβ of 1 μM. Cell viability was determined by the standard MTT assay [48]. After 24 h exposure of cells to the Aβ42 solutions, 100 μL of a 0.5 mg/mL stock solution of MTT in Neurobasal-A was added to each well of primary hippocampal neurons followed by a 3 h incubation at 37° C. The medium was removed and the cells were diluted in DMSO. The relative formazan concentration was measured by determination of the absorbance at 540 nm and 620 nm with an well plate reader photometer. Results were expressed as the percentage of MTT reduction, assuming that the absorbance of control (untreated) cells was 100%, and are the mean of three independent experiments with four replicate wells for each condition. In hippocampal neuronal cultures the statistical significance of changes in different groups was evaluated by one-way analysis of variance (ANOVA). The cell viability results are given in Scheme 4A where it is obvious the great toxicity that Aβ42 induce in primary neurons (approximately 50% of cell viability). However the presence of Re-2 and Re-3 complexes inhibit the induced-neurotixicity of Aβ42 with cell viability rates reaching 95% at the highest tested concentration of 2 μM.

Example 13

Antioxidant Activity of Re-2 and Re-3 Complexes Against ROS

The pathogenesis of Alzheimer's disease is associated with the formation of reactive oxygen species (ROS) and induction of oxidative stress [49, 50] and it is well known that β-amyloid peptide (Aβ) induces ROS production in cell cultures in vitro [51]. In order to determine the antioxidant activity of the compounds of the invention, the fluorescein derivative (DCFH-DA) was used which, when it crosses the cell membrane, it reacts with hydroxyl radicals and becomes fluorescent (DCF). Thus, by this way we are able to monitor the presence of ROS [52]. The antioxidant activity of Re-2 and Re-3 complexes against ROS was studied in primary hippocampal neurons as previously described in Example 12. After incubation with Aβ42 solutions for 24 h, cells were washed with PBS and incubated with 10 μM of DCFH-DA for 30 min at 37° C. in the incubator with 5% $CO_2$. The fluorescence intensity (relative fluorescence unit) of DCF was determined using a well plate reader photometer at the excitation wavelength of 485 nm and emission wavelength of 528 nm.

Figure 4:
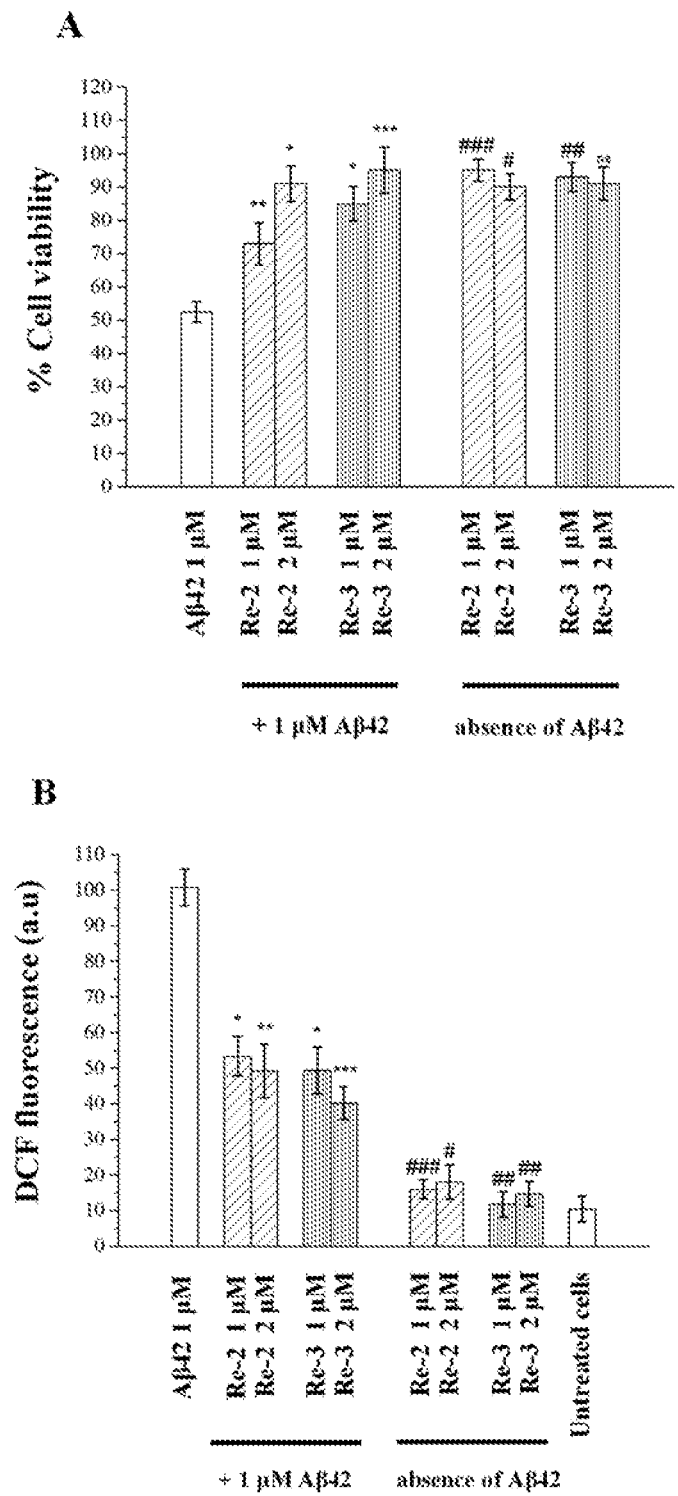
FIG. 4 presents: (A) the effect of complexes Re-2 and Re-3 (1 and 2 μM) on the cytotoxicity induced by Aβ42 in murine primary hippocampal cell lines after a 24 h incubation at 37° C., assessed by means of MTT (Example 12); (B) the effect of complexes Re-2 and Re-3 (1 and 2 μM) upon the generation of ROS induced by Aβ42 in murine primary hippocampal cell lines after a 24 h incubation at 37° C. The evaluation of the amount of generated ROS was performed by means of DCF fluorometric method (Example 13). The reported results (coming from n=3 independent experiments, where each condition was repeated 6 times) are presented as mean of values±SEM. *p≤0.05, p≤0.01, *p≤0.001, ns (not significant)>0.05 for Aβ42 (1 μM) and #p<0.01 and ##p<0.01. ###p<0.001 for cells grown in medium only (control).

The results are shown in FIG. 4B where the high levels of ROS in the presence of plain Aβ42 (strong DCF fluorescence intensity normalized to 100%) and then the great inhibition of ROS generation (>50%) in the presence of Re-2 and Re-3 complexes, are evident.

BIBLIOGRAPHY

1. Pardridge, W. M., *The blood-brain barrier: bottleneck in brain drug development*. NeuroRx, 2005. 2(1): p. 3-14.
2. Wager, T. T., et al., *Strategies to optimize the brain availability of central nervous system drug candidates*. Expert Opin Drug Discov, 2011. 6(4): p. 371-81.
3. Pardridge, W. M., *Alzheimer's disease drug development and the problem of the blood-brain barrier*. Alzheimers Dement, 2009. 5(5): p. 427-32.
4. Hardy, J., *A hundred years of Alzheimer's disease research*. Neuron, 2006. 52(1): p. 3-13.
5. Selkoe, D. J. and J. Hardy, *The amyloid hypothesis of Alzheimer's disease at 25 years*. EMBO Mol Med, 2016. 8(6): p. 595-608.
6. Hardy, J. and D. J. Selkoe, *The amyloid hypothesis of Alzheimer's disease: progress and problems on the road to therapeutics*. Science, 2002. 297(5580): p. 353-6.
7. McKhann, G. M., et al., *The diagnosis of dementia due to Alzheimer's disease: recommendations from the National Institute on Aging-Alzheimer's Association workgroups on diagnostic guidelines for Alzheimer's disease*. Alzheimers Dement, 2011. 7(3): p. 263-9.
8. Montine, T. J., et al., *National Institute on Aging-Alzheimer's Association guidelines for the neuropathologic assessment of Alzheimer's disease: a practical approach*. Acta Neuropathol, 2012. 123(1): p. 1-11.
9. Chen, K. H. and M. G. Cui, *Recent progress in the development of metal complexes as beta-amyloid imaging probes in the brain*. Medchemcomm, 2017. 8(7): p. 1393-1407.
10. Johnson, K. A., et al., *Appropriate use criteria for amyloid PET: a report of the Amyloid Imaging Task Force, the Society of Nuclear Medicine and Molecular Imaging, and the Alzheimer's Association*. Alzheimers Dement, 2013. 9(1): p. e-1-16.
11. Dubois, B., et al., *Timely Diagnosis for Alzheimer's Disease: A Literature Review on Benefits and Challenges*. J Alzheimers Dis, 2016. 49(3): p. 617-31.
12. Ono, M. and H. Saji, *Recent advances in molecular imaging probes for beta-amyloid plaques*. Medchemcomm, 2015. 6(3): p. 391-402.
13. Bernard, J., et al., *Aqueous synthesis of derivatized cyclopentadienyl complexes of technetium and rhenium directed toward radiopharmaceutical application*. Inorganic Chemistry, 2003. 42(4): p. 1014-1022.
14. Cui, M. C., *Past and Recent Progress of Molecular Imaging Probes for beta-Amyloid Plaques in the Brain*. Current Medicinal Chemistry, 2014. 21(1): p. 82-112.
15. Li, Z. J., et al., *Novel Cyclopentadienyl Tricarbonyl Complexes of Tc-99m Mimicking Chalcone as Potential Single-Photon Emission Computed Tomography Imaging Probes for beta-Amyloid Plaques in Brain*. Journal of Medicinal Chemistry, 2013. 56(2): p. 471-482.
16. Jia, J. H., et al., *2-Phenylbenzothiazole conjugated with cyclopentadienyl tricarbonyl [CpM(CO)(3)] (M=Re, Tc-99m) complexes as potential imaging probes for beta-amyloid plaques*. Dalton Transactions, 2015. 44(14): p. 6406-6415.
17. Jia, J. H., et al., *2-Arylbenzothiazoles labeled with [CpRe/Tc-99m(CO)(3)] and evaluated as beta-amyloid imaging probes*. European Journal of Medicinal Chemistry, 2016. 124: p. 763-772.

18. Kiritsis, C., et al., *2-(4'-Aminophenyl)benzothiazole Labeled with Tc-99m-Cyclopentadienyl for Imaging beta Amyloid Plaques*. Acs Medicinal Chemistry Letters, 2017. 8(10): p. 1089-1092.
19. Kim, S. H., et al., *Beyond symptomatic effects: potential of donepezil as a neuroprotective agent and disease modifier in Alzheimer's disease*. British Journal of Pharmacology, 2017. 174(23): p. 4224-4232.
20. Walsh, D. M. and D. J. Selkoe, *A beta oligomers-a decade of discovery*. J Neurochem, 2007. 101(5): p. 1172-84.
21. Belluti, F., et al., *Small-molecule inhibitors/modulators of amyloid-beta peptide aggregation and toxicity for the treatment of Alzheimer's disease: a patent review (2010-2012)*. Expert Opinion on Therapeutic Patents, 2013. 23(5): p. 581-96.
22. Ansari, N. and F. Khodagholi, *Natural Products as Promising Drug Candidates for the Treatment of Alzheimer's Disease: Molecular Mechanism Aspect*. Current Neuropharmacology, 2013. 11(4): p. 414-429.
23. Campagna, F., et al., *Synthesis and biophysical evaluation of arylhydrazono-1H-2-indolinones as beta-amyloid aggregation inhibitors*. European Journal of Medicinal Chemistry, 2011. 46(1): p. 275-84.
24. Datki, Z., et al., *Method for measuring neurotoxicity of aggregating polypeptides with the MTT assay on differentiated neuroblastoma cells*. Brain Res Bull, 2003. 62(3): p. 223-9.
25. Banks, W. A., *Drug delivery to the brain in Alzheimer's disease: consideration of the blood-brain barrier*. Adv Drug Deliv Rev, 2012. 64(7): p. 629-39.
26. Ferlay, J., et al., *Cancer incidence and mortality worldwide: sources, methods and major patterns in GLOBOCAN 2012*. Int J Cancer, 2015. 136(5): p. E359-86.
27. Ostrom, Q. T., et al., *American Brain Tumor Association Adolescent and Young Adult Primary Brain and Central Nervous System Tumors Diagnosed in the United States in 2008-2012*. Neuro Oncol, 2016. 18 Suppl 1: p. i1-i50.
28. Fortin, D., *The blood-brain barrier: its influence in the treatment of brain tumors metastases*. Curr Cancer Drug Targets, 2012. 12(3): p. 247-59.
29. Pitz, M. W., et al., *Tissue concentration of systemically administered antineoplastic agents in human brain tumors*. J Neurooncol, 2011. 104(3): p. 629-38.
30. Antonadou, D., et al., *Phase II randomized trial of temozolomide and concurrent radiotherapy in patients with brain metastases*. J Clin Oncol, 2002. 20(17): p. 3644-50.
31. Weidle, U. H., J. Niewohner, and G. Tiefenthaler, *The Blood-Brain Barrier Challenge for the Treatment of Brain Cancer, Secondary Brain Metastases, and Neurological Diseases*. Cancer Genomics Proteomics, 2015. 12(4): p. 167-77.
32. Santra, A., R. Kumar, and P. Sharma, *Use of 99m-technetium-glucoheptonate as a tracer for brain tumor imaging: An overview of its strengths and pitfalls*. Indian J Nucl Med, 2015. 30(1): p. 1-8.
33. Gao, H. and X. Jiang, *Progress on the diagnosis and evaluation of brain tumors*. Cancer Imaging, 2013. 13(4): p. 466-81.
34. Deutsch, E., et al., *The Chemistry of Rhenium and Technetium as Related to the Use of Isotopes of These Elements in Therapeutic and Diagnostic Nuclear-Medicine*. Nuclear Medicine and Biology, 1986. 13(4): p. 465-477.
35. Bradshaw, T. D. and A. D. Westwell, *The development of the antitumour benzothiazole prodrug, Phortress, as a clinical candidate*. Current Medicinal Chemistry, 2004. 11(8): p. 1009-1021.
36. Kumar, D., et al., *Synthesis and evaluation of anticancer benzoxazoles and benzimidazoles related to UK-1*. Bioorg Med Chem, 2002. 10(12): p. 3997-4004.
37. Shrivastava, N., et al., *Benzimidazole Scaffold as Anticancer Agent: Synthetic Approaches and Structure-Activity Relationship*. Arch Pharm (Weinheim), 2017. 350(6).
38. Xiang, P., et al., *Novel Benzothiazole, Benzimidazole and Benzoxazole Derivatives as Potential Antitumor Agents: Synthesis and Preliminary in Vitro Biological Evaluation*. Molecules, 2012. 17(1): p. 873-883.
39. Nakamura, K., et al., *The behavior of 99mTc-hexamethylpropyleneamineoxime (99mTc-HMPAO) in blood and brain*. Eur J Nucl Med, 1989. 15(2): p. 100-7.
40. Vanbilloen, H. P., B. J. Cleynhens, and A. M. Verbruggen, *Importance of the two ester functions for the brain retention of 99mTc-labelled ethylene dicysteine diethyl ester (99mTc-ECD)*. Nuclear Medicine and Biology, 1998. 25(6): p. 569-75.
41. Schibli, R., et al., *Influence of the denticity of ligand systems on the in vitro and in vivo behavior of Tc-99m (I)-tricarbonyl complexes: A hint for the future functionalization of biomolecules*. Bioconjugate Chemistry, 2000. 11(3): p. 345-351.
42. Neirinckx, R. D., et al., *Tc-99m D,1-Hm-Pao—a New Radiopharmaceutical for Spect Imaging of Regional Cerebral Blood Perfusion*. Journal of Nuclear Medicine, 1987. 28(2): p. 191-202.
43. Bussiere, T., et al., *Morphological characterization of Thioflavin-S-positive amyloid plaques in transgenic Alzheimer mice and effect of passive Abeta immunotherapy on their clearance*. Am J Pathol, 2004. 165(3): p. 987-95.
44. Klunk, W. E., et al., *Uncharged thioflavin-T derivatives bind to amyloid-beta protein with high affinity and readily enter the brain*. Life Sci, 2001. 69(13): p. 1471-84.
45. Jia, J., et al., *2-Phenylbenzothiazole conjugated with cyclopentadienyl tricarbonyl [CpM(CO)3] (M=Re, (99m)Tc) complexes as potential imaging probes for beta-amyloid plaques*. Dalton Trans, 2015. 44(14): p. 6406-15.
46. Hartley, D. M., et al., *Protofibrillar intermediates of amyloid beta-protein induce acute electrophysiological changes and progressive neurotoxicity in cortical neurons*. J Neurosci, 1999. 19(20): p. 8876-84.
47. Nunez, J., *Primary Culture of Hippocampal Neurons from P0 Newborn Rats*. J Vis Exp, 2008(19).
48. Berridge, M. V., P. M. Herst, and A. S. Tan, *Tetrazolium dyes as tools in cell biology: new insights into their cellular reduction*. Biotechnol Annu Rev, 2005. 11: p. 127-52.
49. Gella, A. and N. Durany, *Oxidative stress in Alzheimer disease*. Cell Adh Migr, 2009. 3(1): p. 88-93.
50. Cheignon, C., et al., *Oxidative stress and the amyloid beta peptide in Alzheimer's disease*. Redox Biol, 2018. 14: p. 450-464.
51. Butterfield, D. A., *Amyloid beta-peptide (1-42)-induced oxidative stress and neurotoxicity: implications for neurodegeneration in Alzheimer's disease brain. A review*. Free Radic Res, 2002. 36(12): p. 1307-13.
52. LeBel, C. P., H. Ischiropoulos, and S. C. Bondy, *Evaluation of the probe 2',7'-dichlorofluorescin as an indicator of reactive oxygen species formation and oxidative stress*. Chem Res Toxicol, 1992. 5(2): p. 227-31.

The invention claimed is:

1. A compound according to formula 1 or a pharmaceutically acceptable salt thereof

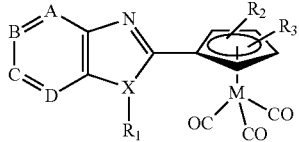

wherein
M is Tc
X is S or O
A is $C-R_A$, B is $C-R_B$, C is $C-R_C$, D is $C-R_D$, wherein $R_A$, $R_C$, $R_D$ are the same or different and are selected from the group consisting of hydrogen, halogen, nitro-, alkyl-, haloalkyl- with 0 to 3 halogen atoms on each carbon atom, aminoalkyl-, alkylamino-, hydroxyl, alkyloxy-, benzyloxy-, aryloxy-, $-SO_2-C(=O)NR_4R_5$, $-C(=S)NR_4R_5$, $-SO_2NR_4R_5$, and $-NC(=O)R_4$, wherein $R_B$ is selected from the group consisting of halogen, alkyl-, haloalkyl- with 0 to 3 halogen atoms on each carbon atom, aminoalkyl-, alkylamino-, hydroxyl, alkyloxy-, benzyloxy-, aryloxy-, $-SO_2-C(=O)NR_4R_5$, $-C(=S)NR_4R_5$, $-SO_2NR_4R_5$, and $-NC(=O)R_4$, wherein $R_4$, $R_5$ are the same or different and are hydrogen or $C_1$-$C_6$ alkyl-
$R_1$ is absent
$R_2$, $R_3$ are the same or different and are selected from hydrogen, $-NR_4R_5$, $-NC(=O)R_4$ wherein $R_4$, $R_5$ are the same or different and are hydrogen or $C_1$-$C_6$ alkyl group.

2. The compound according to claim 1 or a pharmaceutically acceptable salt thereof, wherein $R_2$ and/or $R_3$ is hydrogen.

3. The compound according to claim 1 or a pharmaceutically acceptable salt thereof, wherein M is Tc, A is C—H, C is C—H, D is C—H, $R_2$ is H, $R_3$ is H, and X is S or O.

4. The compound according to claim 3 or a pharmaceutically acceptable salt thereof, wherein Tc is $^{99m}$Tc.

5. A method of diagnosing and/or treating a CNS disease in a subject in need thereof, the method comprising;
administering to the subject a compound according to formula 1 or a pharmaceutically acceptable salt thereof

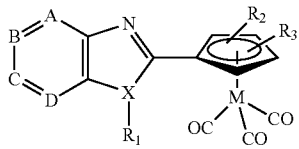

wherein
M is Re, Tc, or other transition metal capable of forming a tricarbonyl cyclopentadienyl entity of the type $CpM(CO)_3^+$
X is S, N, or O
A is $C-R_A$, B is $C-R_B$, C is $C-R_C$, D is $C-R_D$, wherein $R_A$, $R_B$, $R_C$, $R_D$ are the same or different and are selected from the group consisting of hydrogen, halogen, nitro-, alkyl-, haloalkyl- with 0 to 3 halogen atoms on each carbon atom, aminoalkyl-, alkylamino-, hydroxyl, alkyloxy-, benzyloxy-, aryloxy-, $-SO_2-C(=O)NR_4R_5$, $-C(=S)NR_4R_5$, $-SO_2NR_4R_5$, and $-NC(=O)R_4$, wherein $R_4$, $R_5$ are the same or different and are hydrogen or $C_1$-$C_6$ alkyl-
when X is N, $R_1$ is hydrogen, alkyl-, alkenyl-, haloalkyl- with 0 to 3 halogen atoms on each carbon atom, alkoxyalkyl-, cycloalkyl-, or arylalkyl-, whereas when X is S or —O, $R_1$ does not exist
when M is Re and X is N, Rc is selected from the group consisting of halogen, alkyl-, haloalkyl- with 0 to 3 halogen atoms on each carbon atom, aminoalkyl-, alkylamino-, hydroxyl, alkyloxy-, benzyloxy-, aryloxy-, $-SO_2-C(=O)NR_4R_5$, $-C(=S)NR_4R_5$, $-SO_2NR_4R_5$, and $-NC(=O)R_4$
$R_2$, $R_3$ are the same or different and are selected from hydrogen, $-NR_4R_5$, $-NC(=O)R_4$ wherein $R_4$, $R_5$ are the same or different and are hydrogen or $C_1$-$C_6$ alkyl group,
wherein the CNS disease is Alzheimer's disease or CNS cancer.

6. The method according to claim 5, wherein M is Re or Tc.

7. The method according to claim 6, wherein M is Tc.

8. The method according to claim 5, wherein M is Re or Tc, A is C—H, B is C—H, C is C—H, D is C—H, $R_2$ is H, $R_3$ is H, X is S, O, N and when X is N, $R_1$ is H or $CH_3$.

9. The method according to claim 8, wherein Tc is $^{99m}$Tc.

10. A pharmaceutical composition comprising as active ingredient a compound according to claim 1 or a pharmaceutically acceptable salt thereof.

11. The method according to claim 5, wherein the compound according to formula 1 or the pharmaceutically acceptable salt thereof is administered as a pharmaceutical composition.

12. The method according to claim 5, wherein the compound according to formula 1 or the pharmaceutically acceptable salt thereof is administered as a pharmaceutical composition.

13. The compound according to claim 1, wherein $R_4$, $R_5$ are the same or different and are hydrogen or $C_1$-$C_2$ alkyl.

* * * * *